(12) United States Patent
Ie et al.

(10) Patent No.: US 8,114,956 B2
(45) Date of Patent: Feb. 14, 2012

(54) POLYMER HAVING UNIT OBTAINED BY CONDENSATION OF DIFLUOROCYCLOPENTANEDIONE RING AND AROMATIC RING, ORGANIC THIN FILM USING THE SAME, AND ORGANIC THIN FILM DEVICE

(75) Inventors: Yutaka Ie, Suita (JP); Yoshio Aso, Suita (JP); Yoshikazu Umemoto, Suita (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 133 days.

(21) Appl. No.: 12/529,878

(22) PCT Filed: Mar. 5, 2008

(86) PCT No.: PCT/JP2008/053953
§ 371 (c)(1),
(2), (4) Date: Sep. 3, 2009

(87) PCT Pub. No.: WO2008/108405
PCT Pub. Date: Sep. 12, 2008

(65) Prior Publication Data
US 2010/0084640 A1    Apr. 8, 2010

(30) Foreign Application Priority Data
Mar. 7, 2007    (JP) ................. P2007-057751

(51) Int. Cl.
C08G 75/00    (2006.01)
(52) U.S. Cl. .......... 528/380; 528/377; 528/373; 257/40; 257/E51.001; 257/E51.005; 526/243; 428/220
(58) Field of Classification Search .................. 528/380, 528/377, 373; 257/40, E51.005, E51.001; 526/243; 428/220
See application file for complete search history.

(56) References Cited

U.S. PATENT DOCUMENTS
2004/0183068 A1    9/2004  Ong et al.
2004/0186266 A1    9/2004  Jiang et al.

FOREIGN PATENT DOCUMENTS
| EP | 1 279 689 A2 | 1/2003 |
|---|---|---|
| JP | 05-110069 A | 4/1993 |
| JP | 2004-006476 A | 1/2004 |
| JP | 2006-131799 A | 5/2006 |
| JP | 2006-248944 A | 9/2006 |
| JP | 2007-270117 A | 10/2007 |
| WO | 03/010778 A1 | 2/2003 |
| WO | 2007/007735 A1 | 1/2007 |

OTHER PUBLICATIONS

Lan Pham Khanh et al., "First Synthesis of Isothianinhydrin, the Second Thiophene Isostere of Ninhydrin", Synlett, Jun. 22, 1999, pp. 1450-1452, No. 9.

(Continued)

*Primary Examiner* — Randy Gulakowski
*Assistant Examiner* — Shane Fang
(74) *Attorney, Agent, or Firm* — Sughrue Mion, PLLC

(57) ABSTRACT

A polymer having a repeating unit represented by the following general formula (I) and a ferrocene-based reduction potential of −1.5 to −0.5 V as measured by a cyclic voltammetry method

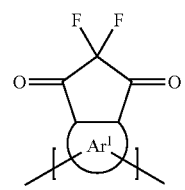

(I)

wherein Ar¹ represents a divalent aromatic hydrocarbon group or a divalent heterocyclic group, and these groups may be substituted by a substituent.

13 Claims, 12 Drawing Sheets

OTHER PUBLICATIONS

Yutaka Ie et al., "Electronegative Oligothiphenes Based on a Hexafluorocyclopentene-Annelated Thiophene Unit", Organic Letters, 2006, pp. 5381-5384, vol. 8, No. 23.

Tsuyoshi Izumi et al., "Synthesis and Spectroscopic Properties of a Series of β-Blocked Long Oligothiophenes up to the 96-mer: Revaluation of Effective Conjugation Length", Journal of American Chemical Society, Jan. 25, 2003, pp. 5286-5287, vol. 125, No. 18.

European Search Report issued in counterpart European Application No. 08721373, dated Nov. 7, 2011.

Zajac, B. et al. "Fluorination with xenon difluoride.27. The effect of catalyst on fluorination of 1,3-diketones and enol acetates", The Journal of Organic Chemistry, vol. 47, No. 3, Jan. 1, 1982, pp. 573-575.

POLYMER HAVING UNIT OBTAINED BY CONDENSATION OF DIFLUOROCYCLOPENTANEDIONE RING AND AROMATIC RING, ORGANIC THIN FILM USING THE SAME, AND ORGANIC THIN FILM DEVICE

TECHNICAL FIELD

The present invention relates to a polymer having a fused unit of a difluorocyclopentanedione ring and an aromatic ring, and an organic thin film and an organic thin film device using this polymer.

BACKGROUND ART

A thin film containing an organic material having an electron transportation property or a hole transportation property is expected to have applications to organic thin film devices such as an organic thin film transistor, an organic solar cell and an optical sensor. A number of research and development on an organic n-type semiconductor are carried out because an organic n-type semiconductor (showing an electron transportation property) is more difficult to be obtained than an organic p-type semiconductor (showing a hole transportation property).

A π-conjugated compound having a fluoroalkyl group has an increased electron accepting property, and thus it may be a promising compound as an electron transporting material such as an organic n-type semiconductor. From this viewpoint, compounds having a thiophene ring, in particular an oligothiophene having a fluoroalkyl group, are studied actively (Patent Documents 1 to 4).

On the other hand, an oligomer having a thiophene ring fused with a cyclopentane ring as a base unit is shown to have a longer effective conjugate chain than an oligothiophene having a linear alkyl group (Non-Patent Document 1).

Patent Document 1: US 2004/186266 A

Patent Document 2: US 2004/183068 A

Patent Document 3: WO 03/010778

Patent Document 4: EP 1279689 A

Non-Patent Document 1: Izumi, T.; Kobashi, S.; Takimiya, K; Aso, Y.; and Otsubo, T: J. Am. Chem. Soc., 2003, 125, 5286

DISCLOSURE OF THE INVENTION

However, heretofore known oligomers as mentioned above do not have a sufficient performance as an organic n-type semiconductor, and thus an organic n-type semiconductor having a further improved electron transportation property is desired.

Accordingly, an object of the present invention is to provide a novel polymer usable as an organic n-type semiconductor having an excellent electron transportation property. Another object of the present invention is to provide an organic thin film containing this novel polymer and an organic thin film device comprising this organic thin film.

In order to accomplish the foregoing objects, the present invention provides a polymer having a repeating unit represented by the following general formula (I) and a ferrocene-based reduction potential of −1.5 to −0.5 V as measured by a cyclic voltammetry method.

[Chemical Formula 1]

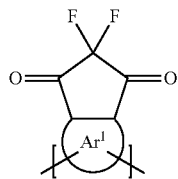

(I)

In formula (I), $Ar^1$ represents a divalent aromatic hydrocarbon group or a divalent heterocyclic group, and these groups may have a substituent.

A polymer having a skeleton as shown above has a good planarity of a π-conjugation between rings, and thus it can be used as an organic n-type semiconductor having an extraordinary excellent electron transportation property. In addition, in this range of the reduction potential, a polymer of the present invention is excellent in electron injection, thereby becoming sufficiently suitable as an n-type semiconductor having excellent electron transportation property. Because this polymer is chemically stable, has a high solubility in an organic solvent, and shows a sufficiently low LUMO, an organic thin film device having an excellent performance may be produced by forming a thin film with it.

In addition, the present invention provides an organic thin film containing a foregoing polymer. Further, the present invention provides an organic thin film device, an organic thin film transistor, an organic solar cell and an optical sensor, which comprise the organic thin film as mentioned above.

An organic thin film, an organic thin film device, an organic thin film transistor, an organic solar cell and an optical sensor, as mentioned above, can have an excellent performance, because they are formed by using a polymer of the present invention having an excellent electric charge transportation property.

Effect of the Invention

According to the present invention, a novel polymer usable as an organic n-type semiconductor having an excellent electron transportation property can be provided. In addition, an organic thin film containing this novel polymer, and an organic thin film device comprising this organic thin film can be provided. In particular, a novel polymer having a structure of 5,5-difluoro-5,6-dihydro-4H-cyclopenta[c]thiophene-4,6-dione has a lowered LUMO level due to an introduction of the 2,2-difluoro-1,3-cyclopentanedione skeleton and an improved solubility in an organic solvent, and keeps a planarity of the π-conjugation. Accordingly, the foregoing novel polymer is useful as an organic n-type semiconductor having an extraordinarily excellent electron transportation property. Further, this novel polymer can be obtained easily by oligomerization or polymerization of a raw material for it. A polymer of the present invention thus obtained is useful especially for production of an organic transistor, an organic solar cell, an optical sensor and the like. In addition, the foregoing polymer is excellent in an electron transportation property, and thus, the organic thin film transistor comprising the foregoing organic thin film usually shows excellent Id-Vg characteristics, the organic solar cell usually shows excellent voltage-current characteristics, and the optical sensor usually shows an excellent ratio of a photocurrent to a dark current.

EXPLANATION OF SYMBOLS

Figure 1:
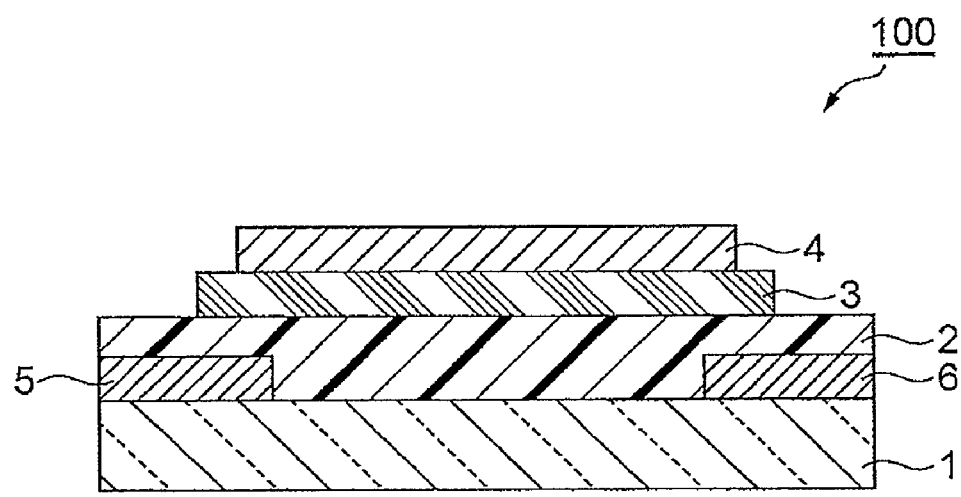
FIG. 1 is a schematic sectional view of the organic thin film transistor according to a first embodiment.

1: Substrate, 2: Active layer, 2a: Active layer, 3: Insulator layer, 4: Gate electrode, 5: Source electrode, 6: Drain electrode, 7: First electrode, 7b: Second electrode, 8: Electric charge generator layer, 100: Organic thin film transistor according to the first embodiment, 110: Organic thin film transistor according to the second embodiment, 120: Organic thin film transistor according to the third embodiment, 130: Organic thin film transistor according to the fourth embodiment, 140: Organic thin film transistor according to the fifth embodiment, 150: Organic thin film transistor according to the sixth embodiment, 160: Organic thin film transistor according to the seventh embodiment, 200: Solar cell according to an embodiment, 300: Optical sensor according to the first embodiment, 310: Optical sensor according to the second embodiment, 320: Optical sensor according to the third embodiment

BEST MODES FOR CARRYING OUT THE INVENTION

Hereinbelow, preferable embodiments of the present invention will be explained in detail with reference to the drawings as necessary. In the drawings, the same element is tagged with the same symbol in order to avoid duplication in explanation. Relationship of positions regarding to right and left, and up and down are based on the positions in the drawings, unless otherwise specifically mentioned. Dimensional ratios in the drawings are not necessarily limited to those shown in the drawings.

A polymer of the present invention is the one having a repeating unit represented by the following general formula (I) and a ferrocene-based reduction potential of −1.5 to −0.5 V as measured by a cyclic voltammetry method. Namely, the polymer contains 1 or more, preferably 2 or more, more preferably 4 or more, and further more preferably 6 or more repeating units represented by the general formula (I) (for example, as a repeating unit represented by the general formula (II) which will be mentioned later), wherein it may contain other repeating units. Here, the upper limit of a repeating unit represented by the general formula (I) in the polymer is usually about 1000.

In the general formula (I), $Ar^1$ represents a divalent aromatic hydrocarbon group or a divalent heterocyclic group, and these groups may have one or more arbitrary substituent(s).

The repeating unit comprising a skeleton represented by the above general formula (I) is preferably a repeating unit represented by the following general formula (II).

[Chemical Formula 2]

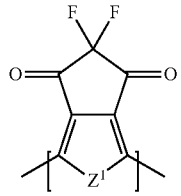

(II)

In the general formula (II), $Z^1$ represents any one of groups shown by the following formulae (i) to (ix). Here, $R^1$, $R^2$, $R^3$ and $R^4$ each independently represents a hydrogen atom or a substituent, and $R^2$ and $R^3$ may be bonded with each other to form a ring.

[Chemical Formula 3]

(i)

(ii)

(iii)

(iv)

(v)

(vi)

(vii)

(viii)

A polymer of the present invention preferably has a repeating unit represented by the general formula (I) and a repeating unit represented by the following general formula (III) which is different from the repeating unit represented by the above general formula (I).

[Chemical Formula 4]

(III)

In formula (III), $Ar^2$ represents a divalent aromatic hydrocarbon group or a divalent heterocyclic group, and these groups may have a substituent.

The ratio of a repeating unit represented by the general formula (I) to a repeating unit represented by the general formula (III) is preferably 10 to 1000 moles, more preferably 25 to 400 moles, and further more preferably 50 to 200 moles of the latter, relative to 100 moles of the former.

In addition, the repeating unit represented by the general formula (III) is preferably a repeating unit represented by the following general formula (IV).

[Chemical Formula 5]

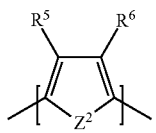

(IV)

In formula (IV), $Z^2$ may be the same as or different from $Z^1$, and represents any one of groups shown by the foregoing formulae (i) to (ix). $R^5$ and $R^6$ each independently represents a hydrogen atom or a substituent, and $R^5$ and $R^6$ may form a ring. Here, $R^1$, $R^2$, $R^3$ and $R^4$ represent the same meaning as before.

Here, the divalent aromatic hydrocarbon group represented by $Ar^1$ or $Ar^2$ is the residual atomic group of a benzene ring or a fused ring from which two hydrogen atoms are extracted, containing usually 6 to 60 carbon atoms, and preferably 6 to 20 carbon atoms. Examples of the fused ring include a naphthalene ring, an anthracene ring, a tetracene ring, a pentacene ring, a pyrene ring, a perylene ring, and a fluorene ring. As the divalent aromatic hydrocarbon group, the residual atomic group of a benzene ring or a fluorene ring from which two hydrogen atoms are extracted is particularly preferable. Here, the divalent aromatic hydrocarbon group may contain a substituent on it. The number of carbon atoms in the divalent aromatic hydrocarbon group does not include the number of carbon atoms in the substituent. Examples of the substituent include a halogen atom, a saturated or an unsaturated hydrocarbon group, an aryl group, an alkoxy group, an aryl alkyl group, an aryloxy group, a monovalent heterocyclic group, an amino group, a nitro group and a cyano group.

Here, the divalent heterocyclic group represented by $Ar^1$ is the residual atomic group of a heterocyclic compound from which two hydrogen atoms are extracted, containing usually 3 to 60, preferably 4 to 60, and more preferably 4 to 20 carbon atoms. Examples of the heterocyclic compound in the foregoing $Ar^1$ include a thiophene ring, a pyrrole ring and a pyridine ring, wherein a thiophene ring is preferable. Here, the divalent heterocyclic group may contain a substituent on it. The number of carbon atoms in the heterocyclic group does not include the number of carbon atoms in the substituent. Examples of the substituent include a halogen atom, a saturated or an unsaturated hydrocarbon group, an aryl group, an alkoxy group, an aryl alkyl group, an aryloxy group, a monovalent heterocyclic group, an amino group, a nitro group and a cyano group.

Here, the divalent heterocyclic group represented by $Ar^2$ is the residual atomic group of a heterocyclic compound from which two hydrogen atoms are extracted, containing usually 3 to 60, and preferably 3 to 20 carbon atoms. Examples of the heterocyclic compound in the foregoing $Ar^2$ are those having a group such as a thiophene ring, 2 to 6 fused thiophene rings (such as a thienothiophene ring and a dithienothiophene ring), a thiazole ring, a pyrrole ring, a pyridine ring, a pyrimidine ring, a pyrazine ring and a triazine ring, wherein a thiophene ring and 2- to 6-fused thiophene rings (such as a thienothiophene ring and a dithienothiophene ring) are preferable. Here, the divalent heterocyclic group may contain a substituent on it. The number of carbon atoms in the divalent heterocyclic group does not include the number of carbon atoms in the substituent. Examples of the substituent include a halogen atom, a saturated or an unsaturated hydrocarbon group, an aryl group, an alkoxy group, an aryl alkyl group, an aryloxy group, a monovalent heterocyclic group, an amino group, a nitro group and a cyano group.

Here, the heterocyclic compound is meant, among organic compounds having a ring structure, by a compound having, as an element to constitute a ring, not only a carbon atom but also a heteroatom such as an oxygen atom, a sulfur atom, a nitrogen atom, a phosphorous atom, a boron atom and a silicon atom in the ring.

A polymer of the present invention contains more preferably a repeating unit represented by the foregoing general formula (II) and a repeating unit represented by the foregoing general formula (III), and further more preferably a repeating unit represented by the foregoing general formula (II) and a repeating unit represented by the foregoing general formula (IV). By setting the composition as mentioned above, a selection range of solubility, mechanical, thermal, or electronic characteristics of the polymer may be made wider.

From a viewpoint of increase in solubility in an organic solvent, the repeating unit represented by the general formula (III) or (IV) preferably contains a substituent. The substituent is preferably a long chain alkyl group having 3 to 20 carbon atoms or a long chain alkoxy group having 3 to 20 carbon atoms. The foregoing long chain alkyl group or long chain alkoxy group may be branched.

As to the sequence of the repeating units, it is preferable that the repeating unit represented by the general formula (III) or (IV) be located next to the repeating unit represented by the general formula (I) or (II), and more preferably the repeating unit represented by the general formula (III) or (IV) be located at the both sides of the repeating unit represented by the general formula (I) or (II). The structure in which the repeating unit represented by the general formula (I) or (II) is arranged alternately is also preferable. In the case when the repeating unit represented by the general formula (IV) is located next to the repeating unit represented by the general formula (I) or (II), in the ring having $Z^2$ in the repeating unit represented by the general formula (IV), the carbon atom next to the carbon atom which forms a bond to the adjacent repeating units represented by the general formula (I) or (II) preferably does not contain a substituent. In addition, the ring having $Z^2$ is preferably a 5-membered ring.

A polymer of the present invention is expected to have a high electron transportation property as an organic n-type semiconductor. To increase this effect, it is preferable to have an electron-withdrawing group as the substituent, also in view of lowering a LUMO level. Accordingly, it is important that the repeating unit represented by the general formula (I) or (II) have a fluorine atom or a carbonyl group. A polymer having the repeating unit as mentioned above can be suitably used for a thin film material used in an organic thin film device as an organic n-type semiconductor. Especially, an oligomer or a polymer which is a polymer of the present invention having a thiophene skeleton expect to contribute to improvement in a performance as an organic semiconductor and reduction in production cost because of not only a lowered LUMO level due to introduction of the 2,2-difluoro-1,3-cyclopentanedione skeleton but also an increase in solubility in an organic solvent and retention of a planarity of the π-conjugation. An organic thin film device of the present invention can have a high performance because it comprises an organic thin film containing the oligomer or the polymer which is a polymer of the present invention having the 2,2-difluoro-1,3-cyclopentanedione skeleton.

$Z^1$ in the general formula (II) and $Z^2$ in the general formula (IV) are preferably the group represented by the foregoing formula (i), (ii), (iii), (viii) or (ix), more preferably the group represented by the formula (i), (ii), or (iii), and particularly preferably the group represented by the formula (i). A thiophene ring, a furane ring and a pyrrole ring have, in particular a thiophene ring has distinguishing electric characteristics, and thus, when fused with a hexafluorocyclopentane ring and the like, an expression of novel electric characteristics not known before may be expected.

$R^1$ to $R^6$ in formulae (iii), (viii) and (ix), and the general formula (IV) each independently represents a hydrogen atom or a substituent, and $R^2$ and $R^3$, or $R^5$ and $R^6$ may form a ring.

It is preferable that $R^1$ to $R^6$ each independently represent a hydrogen atom, a halogen atom, a linear or a branched short molecular chain, a monovalent cyclic group (this cyclic group may be a single or a fused ring, a carbon or a heterocyclic ring, saturated or unsaturated, and contain a substituent or not), an electron-donating group, or an electron-withdrawing group.

In addition, it is more preferable that $R^1$ to $R^6$ each independently represent a hydrogen atom, a halogen atom, a linear or a branched short molecular chain, a monovalent cyclic group having 3 to 60 carbon atoms (this cyclic group may be a single or a fused ring, a carbon or a heterocyclic ring, saturated or unsaturated, and contain a substituent or not), a saturated or an unsaturated hydrocarbon group, a hydroxy group, an alkoxy group, an alkanoyl oxy group, an amino group, an oxy amino group, an alkyl amino group, a dialkyl amino group, an alkanoyl amino group, a cyano group, a nitro group, a sulfo group, an alkyl group substituted with one or more halogen atom(s), an alkoxy sulfonyl group (its alkyl group may be substituted with one or more halogen atom(s)), an alkyl sulfonyl group (its alkyl group may be substituted with one or more halogen atom(s)), a sulfamoyl group, an alkyl sulfamoyl group, a carboxyl group, a carbamoyl group, an alkyl carbamoyl group, an alkanoyl group, or an alkoxy carbonyl group.

The halogen atoms in the present invention include a fluorine atom, a chlorine atom, a bromine atom and an iodine atom.

There is no restriction on the alkyl group, and examples of it include a methyl group, an ethyl group, an n-propyl group, an isopropyl group, an n-butyl group, an isobutyl group, a sec-butyl group and a tert-butyl group. The same is true for the groups containing the alkyl group in it (for example, the alkoxy group, the alkyl amino group, the alkoxy carbonyl group and the like).

There is no restriction on the unsaturated hydrocarbon group, and examples of it include a vinyl group, a 1-propenyl group, an allyl group, a propargyl group, an isopropenyl group, a 1-butenyl group and a 2-butenyl group.

There is no particular restriction in the alkanoyl group, and examples of it include a formyl group, an acetyl group, a propionyl group, an isobutyryl group, a valeryl group and an isovaleryl group. The same is true for the groups containing the alkanoyl group in their structure (for example, the alkanoyl oxy group, the alkanoyl amino group and the like). Here, the alkanoyl group having one carbon atom is meant by a formyl group, and the same is true for the group containing the alkanoyl group in its structure.

A polymer of the present invention needs to contain a repeating unit represented by the general formula (I) or (II), and may contain two or more repeating units represented by the general formula (I) or (II). In addition to the repeating unit represented by the general formula (I) or (II), the polymer may contain a repeating unit represented by the general formula (III) or (IV), or two or more repeating units represented by the general formula (III) or (IV). A polymer of the present invention preferably contain 4 or more (further 6 or more) repeating units represented by the general formula (I) or (II).

A polymer of the present invention, a polymer containing one or more repeating unit(s) represented by the general formula (I) or (II), preferably contain 4 or more (further 6 or more) repeating units represented by any of the general formulae (I), (II), (III) and (IV). Further, a polymer of the present invention, a polymer containing two or more repeating units represented by the general formula (I) or (II), preferably contain 4 or more (further 6 or more) repeating units represented by any of the general formulae (I), (II), (III) and (IV). The polymer with the total number of the repeating unit being 4 or more has better characteristics in electron transportation and the like as compared with a polymer with the total number of the repeating unit being 3 or less. This may be attributable to an improved planarity because of a sufficiently long conjugation chain in the polymer when the total number of the repeating unit is 4 or more. Here, the upper limit of the total number of the repeating unit represented by the general formulae (I), (II), (III) and (IV) in the polymer is usually about 1000.

Figure 12:
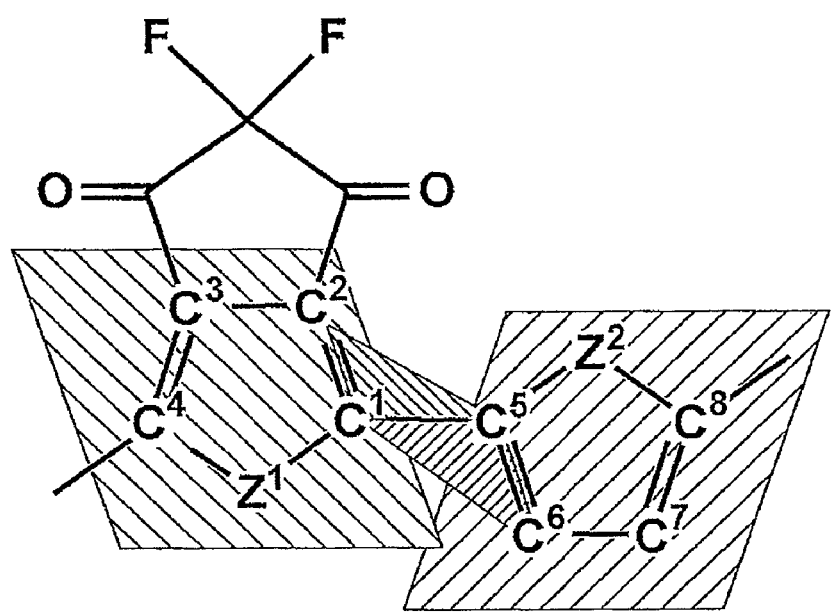
FIG. 12 is a drawing showing a dihedral angle formed by a ring of a repeating unit represented by the general formula (II) and a ring of a repeating unit represented by the general formula (IV).

In the case that the total number of the repeating unit represented by the general formula (I) or (II) is 4 or more, or the total number of the repeating unit represented by the general formula (I) or (II) and the repeating unit represented by the general formula (III) or (IV) is 4 or more, when the repeating unit represented by the general formula (I) or (II) is located next to the repeating unit represented by the general formula (III) or (IV), a dihedral angle formed by aromatic rings or heterocyclic rings by themselves located next to each other can be made small, thereby improving a planarity within a molecule easily, and this, in turn, widens the π-conjugation within a molecule and lowers an LUMO level, resulting in improvement in an electron transportation property, and thus it is preferable. Here, the dihedral angle is defined as the angle of 0 to 90 degrees (both inclusive) among the angles formed by a plane including an aromatic ring represented by the general formula (I) or (II) and a plane including an aromatic ring boding to next to it. In the case as mentioned above, the dihedral angle is usually 0 to 45 degrees, typically 0 to 40 degrees, and more typically 0 to 30 degrees. FIG. 12 is a drawing to show the dihedral angle formed by a ring in the repeating unit represented by the general formula (II) and a ring in the repeating unit represented by the general formula (IV). In FIG. 12, the dihedral angle is meant by the angle formed by a plane of $C^2$-$C^1$-$C^5$ and a plane of $C^1$-$C^5$-$C^6$. In view of improving an electron transportation property, it is preferable that a polymer of the present invention be represented by the following general formulae (V), (VI), (VII) and (VIII).

[Chemical Formula 6]

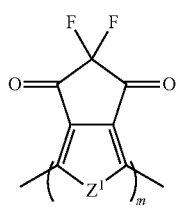
(V)

[Chemical Formula 7]

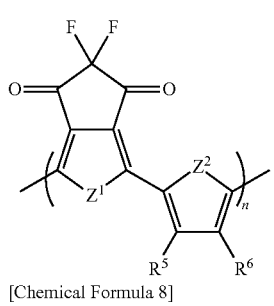
(VI)

[Chemical Formula 8]

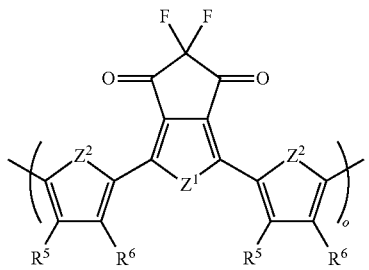
(VII)

[Chemical Formula 9]

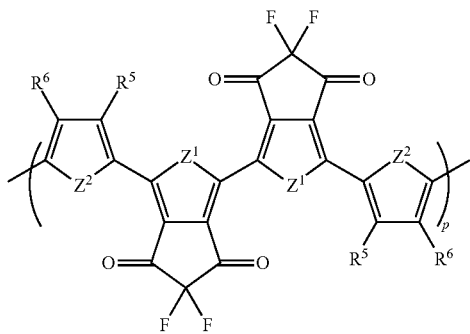
(VIII)

Here, $Z^1$, $Z^2$, $R^5$ and $R^6$ represent the same meanings as before, and $Z^1$, $Z^2$, R and $R^6$ existing in plurality may be the same or different with each other. m represents an integer of 1 to 500, preferably an integer of 1 to 20. n represents an integer of 1 to 500, preferably an integer of 1 to 20. o represents an integer of 1 to 500, preferably an integer of 1 to 10. p represents an integer of 1 to 500, preferably an integer of 1 to 10. Among them, it is particularly preferable that all of $Z^1$ and $Z^2$ be sulfur atoms.

When a polymer of the present invention has a polymerization active group in its terminal, it can also be used as a polymer precursor. The polymerization active group include a halogen atom, an alkyl sulfonate group, an aryl sulfonate group, an aryl alkyl sulfonate group, a dialkoxy boryl group (a borate ester group), a sulfonium methyl group, a phosphonium methyl group, a phosphonate methyl group, a monohalogenated methyl group, a dihydroxy boryl group (a boric acid group), a formyl group, a trialkyl stannyl group or a vinyl group, and a halogen atom, dialkoxy boryl group and a trialkyl stannyl group are preferable.

In the case a polymer of the present invention being used as an organic thin film, if a polymerization active group in its terminal is remained as it is, there is a possibility that characteristics and sustainability of the polymer as a device is decreased, and thus the polymerization active group may be protected by a stable group.

Examples of the terminal group include, in addition to a hydrogen atom and a fluorine atom, an alkyl group, an alkoxy group, an acyl group, a carboamide group, an aryl group, a monovalent heterocyclic group (wherein, hydrogen atoms of these groups may be fully or partially substituted with a fluorine atom), an electron-withdrawing group such as a cyano group, a nitro group, a sulfo group and a carboxyl group, or an electron-donating group such as a hydroxyl group and an amino group. In view of improving an electron transportation property, an electron-withdrawing group such as a fluoroalkyl group, a fluoroalkoxy group, a fluoroaryl group and a cycano group are preferable, wherein the group whose hydrogen atoms are totally substituted with fluorine atoms, namely a perfluoroalkyl group, a perfluoroalkoxy group and a perfluorophenyl group are more preferable. Those having a continuous conjugated bond to a main chain conjugate structure are also preferable, and a structure in which the bond is made to an aryl group or a monovalent heterocyclic group via a carbon-carbon bond may be mentioned as its example.

It is preferable that a polymer of the present invention has the repeating unit represented by the following general formula (IIa), and the repeating unit represented by the following general formula (IVa) and/or the repeating unit represented by the following general formula (XX). The polymer having the repeating unit like this has a ferrocene-based reduction potential of −1.5 to −0.5 V as measured by a cyclic voltammetry method, and is even more excellent in the electron transportation property.

[Chemical Formula 10]

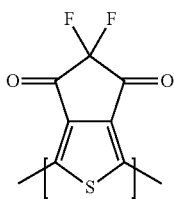
(IIa)

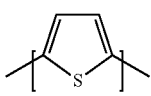
(IVa)

[Chemical Formula 11]

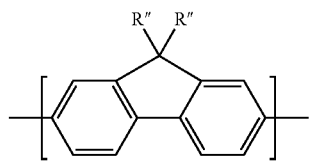
(XX)

Here, R″ represents a hydrogen atom, a fluorine atom, an alkyl group or an aryl group.

Examples of particularly preferable polymers among the polymers of the present invention are shown by the following general formulae (1) to (20). The repeating units in the brackets of the following general formulae (19) and (20) may form a random copolymer formed by random bonding, an alternating copolymer formed by alternate bonding, or a block copolymer formed by bonding in blocks.

[Chemical Formula 12]

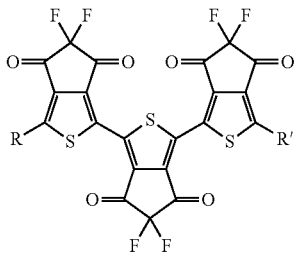
(1)

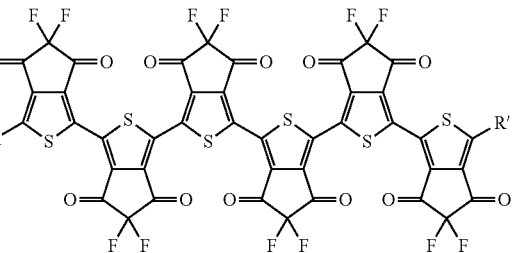
(2)

[Chemical Formula 13]

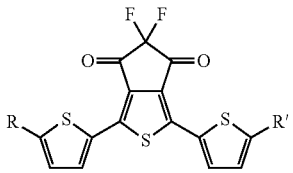
(3)

[Chemical Formula 14]

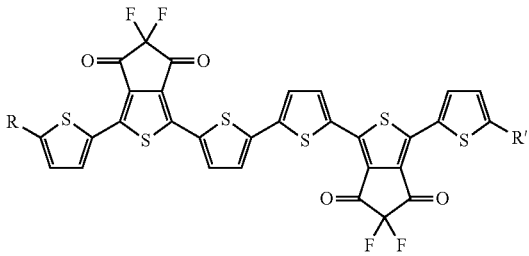
(4)

[Chemical Formula 15]

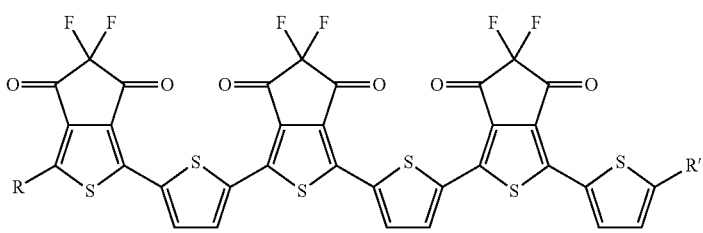
(5)

[Chemical Formula 16]

[Chemical Formula 17]

-continued
(6)
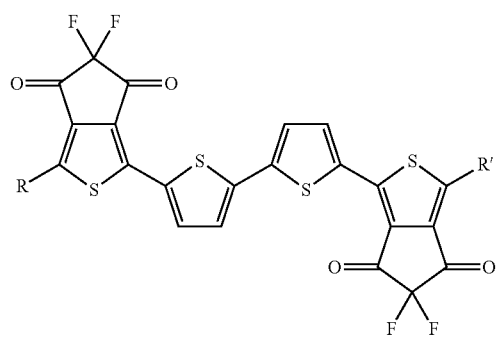
[Chemical Formula 18]
(7)
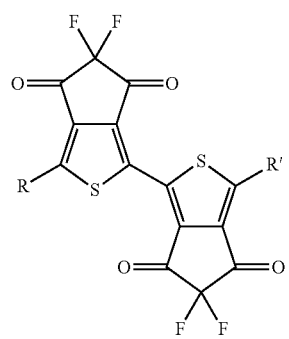
[Chemical Formula 19]
(8)
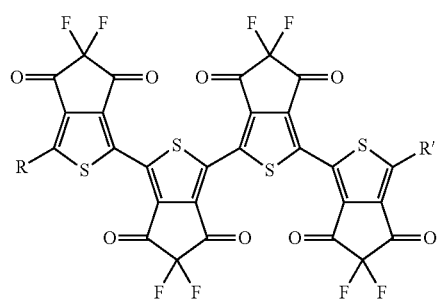
[Chemical Formula 20]
(9)
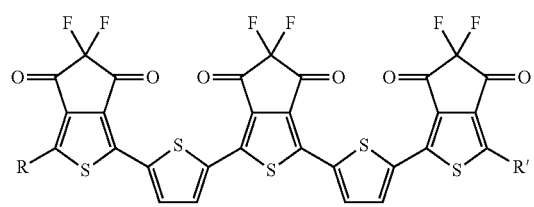
(10)
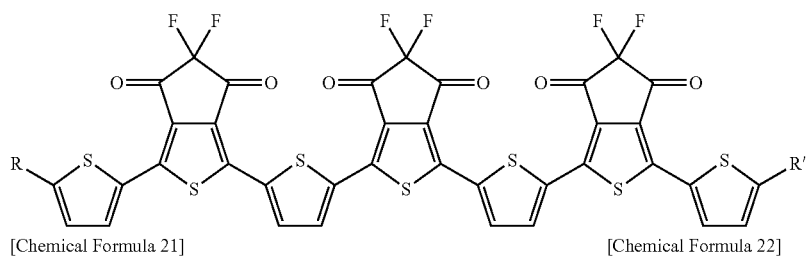
[Chemical Formula 21]    [Chemical Formula 22]
(11)
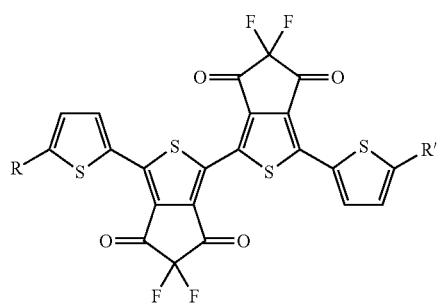
(12)
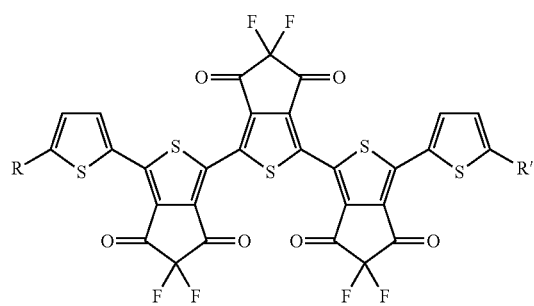

[Chemical Formula 23]
(13)
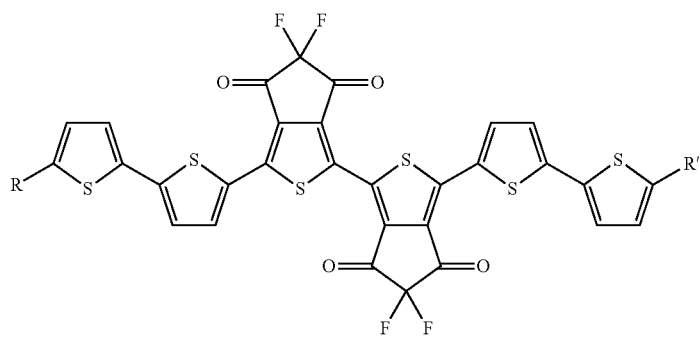
[Chemical Formula 24]
(14)
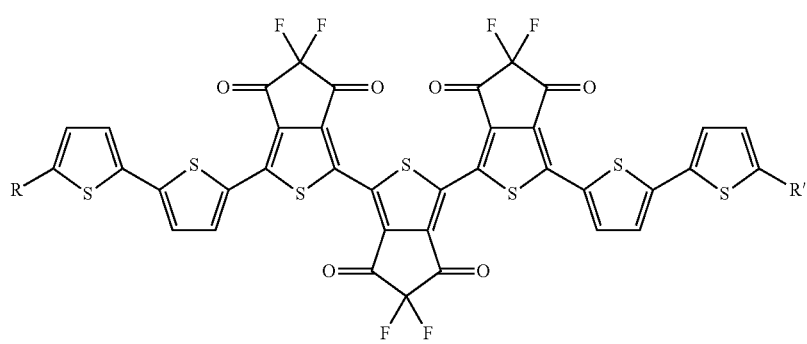
[Chemical Formula 25]
(15)
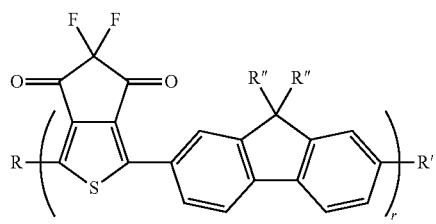
[Chemical Formula 26]
(16)
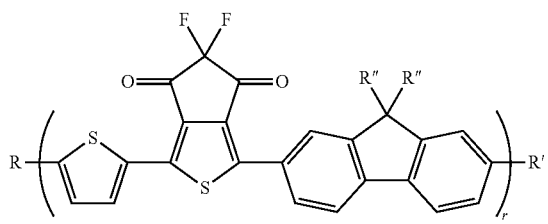
[Chemical Formula 27]
(17)
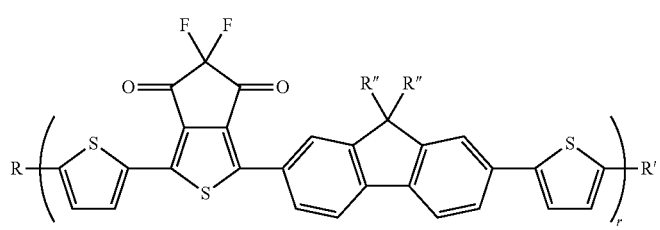

[Chemical Formula 28]

(18)

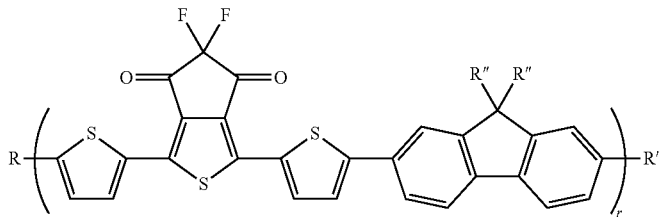

[Chemical Formula 29]

(19)

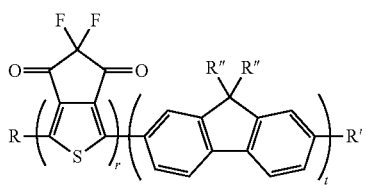

[Chemical Formula 30]

(20)

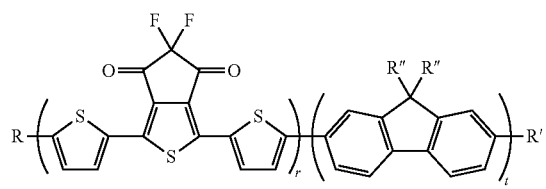

Here, R and R' represent a terminal group, and may be the same or different, exemplified by the foregoing terminal groups. R and R' represent preferably a fluoroalkyl group, and more preferably a perfluoroalkyl group. Each R" independently represents a hydrogen atom or an arbitrary substituent, and is preferably an alkyl group, an alkoxy group, an aryl group and an aryl alkyl group, and more preferably an alkyl group and an aryl group. Each r and t may be selected arbitrarily depending on a method for forming an organic thin film by using the polymer. If the polymer has a subliming property, it may be made to an organic thin film by a vapor growth method such as a vacuum deposition method. In this case, r and/or t is preferably an integer of 1 to 10, more preferably an integer of 2 to 10, and further more preferably an integer of 2 to 5. On the other hand, in the case that an organic thin film is formed by coating a solution of the polymer dissolved in an organic solvent, r and/or t is preferably an integer of 3 to 500, more preferably an integer of 6 to 300, and further more preferably an integer of 20 to 200. In view of uniformity of a film when it is formed by the coating, the number-average molecular weight of the polymer converted to polystyrene is preferably $1 \times 10^3$ to $1 \times 10^8$, and more preferably $1 \times 10^4$ to $1 \times 10^6$.

A polymer of the present invention has a ferrocene-based reduction potential of preferably −1.5 to −0.5 V, and more preferably −1.4 to −1.0 V as measured by an electric chemical method (a cyclic voltammetry method). When the reduction potential is within the foregoing range, a polymer of the present invention has an excellent electron injection property, thereby giving a sufficiently suitable n-type semiconductor having an excellent electron transportation property. The reduction potential can be measured by the method as described below. Here, a supporting electrolyte, an organic solvent and electrodes for use in measurement are not limited to those examples shown below, and any of arbitrarily selected ones may be used as far as the same level of measurement can be made.

A material to be measured is dissolved (about 0.1 to 2 mM) into an organic solvent containing about 0.1 mol/liter of, for example, tetrabutyl ammonium perchlorate, tetrabutyl ammonium hexafluorophosphate and the like, as the supporting electrolyte. The solution thus obtained is deoxygenized by bubbling with a dry nitrogen, degassing under vacuum, irradiation of an ultrasonic wave or the like, and then an electrolytic reduction is carried out, starting from an electrically neutral state with a sweeping rate of 100 mV/second, by using, for example, a platinum electrode or a glassy carbon electrode as a work electrode, and, as a counter electrode, for example, a platinum electrode. An oxidation (or reduction) potential of the material to be measured is obtained by comparing the electric potential at the first peak detected in the electric reduction to the oxidation-reduction potential of a standard material such as ferrocene. The reduction potential in the present invention is the value obtained by converting the oxidation (or reduction) potential measured as mentioned above to that of a ferrocene standard.

Then, a method for producing a polymer of the present invention will be explained. The polymer may be produced by reacting the compounds represented, for example, by the following general formulae (IXa), (Xa), (XIa), (XIIa), (IXb), (Xb), (XIb) and (XIIb) (hereinafter, they are shown by (IXa) to (XIIa) and (IXb) to (XIIb)) as raw materials.

[Chemical Formula 31]

(IXa)

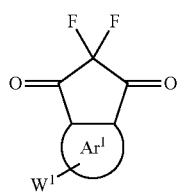

(IXb)

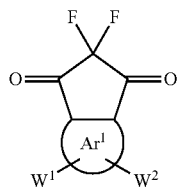

[Chemical Formula 32]

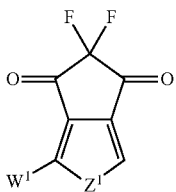
(Xa)

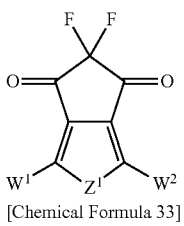
(Xb)

[Chemical Formula 33]

W¹—Ar² (XIa)

W¹—Ar²—W² (XIb)

[Chemical Formula 34]

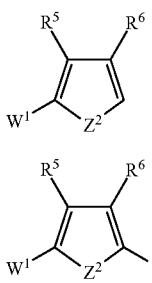
(XIIa)

(XIIb)

$Ar^1$, $Ar^2$, $Z^1$, $Z^2$, $R^5$ and $R^6$ in the above formulae (IXa) to (XIIa) and (IXb) to (XIIb) represent the same meanings as before. Each $W^1$ and $W^2$ independently represents a halogen atom, an alkyl sulfonate group, an aryl sulfonate group, an aryl alkyl sulfonate group, a dialkoxy boryl group, a sulfonium methyl group, a phosphonium methyl group, a phosphonate methyl group, a monohalogenated methyl group, a dihydroxy boryl group, a formyl group, a trialkyl stannyl group or a vinyl group.

In view of facile synthesis and reaction of the compounds represented by the general formulae (IXa) to (XIIa) and (IXb) to (XIIb), it is preferable that each of $W^1$ and $W^2$ independently be a halogen atom, an alkyl sulfonate group, an aryl sulfonate group, an aryl alkyl sulfonate group, a dialkoxy boryl group, a dihydroxy boryl group or a trialkyl stannyl group.

Reaction methods used for production of a polymer of the present invention include a method using a Suzuki coupling reaction, a method using a Grignard reaction, a method using a Stille reaction, a method using a Ni(0) catalyst, a method using an oxidant such as $FeCl_3$, a method using an oxidation reaction of an anion, a method using palladium acetate and an organic base, a method involving an oxidative coupling of a lithio body prepared from an a-unsubstituted or a halogen body, a method using an electric chemical oxidation reaction, or a method involving decomposition of an intermediate compound having an appropriate leaving group.

Among them, a method using a Suzuki coupling reaction, a method using a Grignard reaction, a method using a Stille reaction, a method using a Ni(0) catalyst, a method using an oxidation reaction of an anion, and a method using palladium acetate and an organic base are preferable in view of easiness in structure control, availability of raw materials, and simplicity in reaction operations.

In the case of a Suzuki coupling reaction, the reaction is carried out by using a catalyst such as palladium [tetrakis (triphenylphosphine)] and palladium acetates, wherein an inorganic base such as potassium carbonate, sodium carbonate and barium hydroxide, an organic base such as triethylamine, or an inorganic salt such as cesium fluoride is added for the reaction in the amount of one equivalent or more, preferably 1 to 10 equivalents, relative to a monomer. The reaction may be carried out also in a two-phase system by using an aqueous solution containing an inorganic salt. Examples of the solvent to be used include N,N-dimethyl formamide, toluene, dimethoxy ethane and tetrahydrofurane. Reaction temperature is preferably about 50 to 160° C., though dependent on the solvent used. Reflux by heating at a temperature near a boiling point of the used solvent may also be allowed. Reaction time is about 1 to 200 hours. Suzuki coupling reaction is described, for example, in Chemical Reviews, Vol. 95, p. 2457 (1995).

The reaction using a Ni(0) catalyst will be explained. There are the method in which a zero-valent nickel complex is used as the nickel catalyst and the method in which a zero-valent nickel is formed in situ by reacting a nickel salt in the presence of a reducing agent. Examples of the zero-valent nickel complex include bis(1,5-cyclooctadiene)nickel(0), (ethylene)bis (triphenylphosphine)nickel(0) and tetrakis(triphenylphosphine)nickel. Among them, bis(1,5-cyclooctadiene)nickel(0) is preferable in view of its versatility and low price.

In addition, it is preferable to add a neutral ligand into the foregoing reaction to increase a yield. Here, the neutral ligand is meant by the ligand not having an anion or a cation, and examples of it include a nitrogen-containing ligand such as 2,2'-bipyridyl, 1,10-phenanthroline, methylene bisoxazoline and N,N'-tetramethyl ethylenediamine, and a tertiary phosphine ligand such as triphenyl phosphine, tritolyl phosphine, tributyl phosphine and triphenoxy phosphine. Among them, a nitrogen-containing ligand is preferable in view of its versatility and low price, in particular 2,2'-bipyridyl is preferable because of its high reactivity and reaction yield. Especially, a system formed of bis(1,5-cyclooctadiene)nickel(0) added with 2,2'-bipyridyl as the neutral ligand is preferable in view of a high reaction yield of the polymer. In the method of making a zero-valent nickel in the system, examples of the nickel salt include nickel chloride and nickel acetate. Examples of the reducing agent include zinc, sodium hydride, hydrazine and its derivative, and lithium aluminum hydride. In addition, ammonium iodide, lithium iodide or potassium iodide may be used as an additive as appropriate.

In the case of a Stille reaction, an organic tin compound is reacted as a monomer by using a catalyst, for example, palladium [tetrakis(triphenylphosphine)], palladium acetates or the like. Examples of the solvent to be used include N,N-dimethyl formamide, toluene, dimethoxy ethane and tetrahydrofurane. Reaction temperature is preferably about 50 to 160° C., though dependent on the solvent used. Reflux by heating at a temperature near a boiling point of the used solvent may also be allowed. Reaction time is about 1 to 200 hours.

In the case of a method using an oxidation reaction of an anion, a monomer of a halogen- or a hydrogen-substitute is used to react with n-butyl lithium to obtain a lithio body, which is then treated with an oxidizing agent such as copper (II) bromide, copper (II) chloride and acetylacetonato iron (III). Examples of the solvent to be used include toluene, dimethoxy ethane, tetrahydrofurane, hexane, heptane and octane. Reaction temperature is preferably about 50 to 160° C., though dependent on the solvent used. Reflux by heating at a temperature near a boiling point of the used solvent may also be allowed. Reaction time is about 5 minutes to 200 hours.

In the case of a method using palladium acetate and an organic base, a halogen-substitute is reacted as a monomer by using palladium (II) acetate and an organic base such as diisopropyl amine and triethyl amine. Examples of the solvent to be used include N,N-dimethyl formamide, toluene, dimethoxy ethane and tetrahydrofurane. Reaction temperature is preferably about 50 to 160° C., though dependent on the solvent used. Reflux by heating at a temperature near a boiling point of the used solvent may also be allowed. Reaction time is about 5 minutes to 200 hours.

In the case of producing an oligomer having 4 or more repeating units as the polymer of the present invention, a reaction may be carried out by selecting a combination of a substituent participating in a polycondensation of a corresponding monomer and a polymerization reaction to be used. For example, there may be mentioned the method in which an oligomer having 2 or more repeating units is synthesized, a polymerization active group is introduced into this oligomer to obtain a monomer, and then a polymerization is done among the foregoing monomers by themselves or between the foregoing monomer and another monomer.

In the case of synthesizing a polymer having a high molecular weight as the polymer of the present invention, a monomer having 2 or more polymerization active groups may be reacted by selecting a combination of a substituent participating in a polycondensation of this monomer and a polymerization reaction to be used. In order to obtain a high degree of polymerization without impairing solubility into an organic solvent, it is preferable to use a monomer having 2 polymerization active groups, such as those represented by the foregoing general formulae (IXb) to (XIIb). It is preferable that, in addition to a monomer including the general formula (IXb) or (Xb), a monomer including the general formula (XIb) or (XIIb) be used simultaneously. Further, it is more preferable that the monomer including the general formula (XIb) or (XIIb) contain a substituent.

In the case that a polymer of the present invention has an asymmetrical skeleton in its repeating unit, there is a direction of the repeating unit in the polymer. In order to control the direction of the repeating unit, for example, there may be mentioned a polymerization method in which the direction of the repeating unit is controlled by selecting a combination of a substituent participating in a polycondensation of a corresponding monomer and a polymerization reaction to be used.

In the case that a sequence of two or more repeating units is controlled in a polymer of the present invention, there may be exemplified by the method in which polymerization is carried out after an oligomer having a part or all of the repeating units in the intended sequence is synthesized, and the method in which a polymerization is carried out with control of a sequence of repeating units by selecting a substituent ing in a polycondensation of each monomer and a polymerization reaction to be used.

In the case that $Z^1$ and $Z^2$ in the general formula (II) or (IV) in a polymer of the present invention represent (i), (vi) or (vii), it is preferable to use a method using a Stille reaction.

In the case that a random copolymer is synthesized in a polymer of the present invention, there may be exemplified by the method in which the polymerization is carried out by selecting the same polymerization active groups as the substituent participating in a polycondensation of each monomer to be used and selecting a polymerization reaction to be used. For example, there may be mentioned the method in which a bromine is selected as the polymerization active group and a Ni(0) catalyst is used.

In the case that an alternating copolymer represented by the general formulae (15) to (18) is synthesized in the present invention, there may be exemplified by the method in which the polymerization is carried out with control of a sequence of repeating units by using at least two kinds of monomers, wherein a different polymerization active group is selected for a substituent participating in a polycondensation of each monomer to be used, and a polymerization reaction to be used is selected. For example, there may be mentioned the method in which a Suzuki coupling reaction is carried out with a bromine being selected as one polymerization active group and a dialkoxy boryl group being selected as another polymerization active group, and the method in which a Stille reaction is carried out with a bromine being selected as one polymerization active group and a trialkyl stannyl group being selected as another polymerization active group.

In the case that a block copolymer represented by the general formula (19) or (20) is synthesized in the present invention, there may be mentioned the method in which, after a reaction to form a random copolymer or an alternating copolymer, another monomer is newly added and then polymerized without deactivating a terminal polymerization active group.

In the case that a compound represented by the foregoing general formulae (IXa) to (XIIa) and (IXb) to (XIIb) is used as the monomer, a reaction may be carried out, as appropriate, by dissolving it in an organic solvent and using, for example, an alkali and an appropriate catalyst, at a temperature of equal to or above a melting point and below or equal to a boiling point of the organic solvent.

Generally, it is preferable to carry out a reaction under an inert atmosphere in order to avoid a side reaction by fully deoxygenating an organic solvent used, though dependent on a compound and a reaction used. Similarly, it is preferable to carry out a dehydration treatment. However, the same is not applicable to a two-phase reaction using water such as a Suzuki coupling reaction.

In order to facilitate a reaction, it is preferable to add an alkali as appropriate and an appropriate catalyst. These may be selected according to a reaction to be used. It is preferable that the foregoing alkali or catalyst be sufficiently dissolved in a solvent used in the reaction.

In the case that a polymer of the present invention is used as a material for an organic thin film device, it is preferable that a monomer be purified prior to a reaction by such a method as distillation, purification by sublimation, and recrystallization, which is then followed by polymerization, because the purity affects device properties. In addition, it is preferable that a purification treatment such as reprecipitation and fractionation by a chromatography be done after the polymer is synthesized.

Examples of the foregoing solvent include saturated hydrocarbons such as pentane, hexane, heptane, octane and cyclohexane; unsaturated hydrocarbons such as benzene, toluene, ethyl benzene and xylene; halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane; halogenated unsaturated hydrocarbons such as chlorobenzene, dichlorobenzene and trichlorobenzene; alcohols such as methanol, ethanol, propanol, isopropanol, butanol and t-butyl alcohol; carboxylic acids such as formic acid, acetic acid and propionic acid; ethers such as dimethyl ether, diethyl ether, methyl t-butyl ether, tetrahydrofurane, tetrahydropyran and dioxane; inorganic acids such as hydrochloric acid, hydrobromic acid, hydrofluoric acid, sulfuric acid and nitric acid. The foregoing solvents may be used singly or in a combination of two or more kinds.

After the reaction, the product can be obtained by a usual post-treatment such as extraction with an organic solvent after quenching by water followed by solvent removal by distillation can be. Isolation and purification of the product may be done by such methods as fractionation by a chromatography and recrystallization.

Then, an organic thin film of the present invention will be explained. An organic thin film of the present invention contains the polymer of the present invention as mentioned above.

Film thickness of the organic thin film is usually about 1 nm to 100 µm, preferably 2 to 1000 nm, more preferably 5 to 500 nm, and particularly preferably 20 to 200 nm.

An organic thin film may contain the foregoing polymer singly or two or more kinds. In order to improve an electron transportation property or a hole transportation property of the organic thin film, its mixture with a low molecular weight compound or a polymer compound having an electron transportation property or a hole transportation property (an electron transporting material and a hole transporting material) other than the foregoing polymers may be used.

Hole transportation materials heretofore known may be used, including a pyrazoline derivative, an aryl amine derivative, a stilbene derivative, a triaryl diamine derivative, an oligothiophene and its derivative, a polyvinyl carbazole and its derivative, a polysilane and its derivative, a polysiloxane derivative having an aromatic amine at its side chain or main chain, polyaniline and its derivative, polythiophene and its derivative, polypyrrol and its derivative, a polyarylene vinylene and its derivative, and polythienylene vinylene and its derivative. Electron transportation materials heretofore known may be used, including an oxadiazole derivative, anthraquinodimethane and its derivative, benzoquinone and its derivative, naphthoquinone and its derivative, anthraquinone and its derivative, tetracyano anthraquinodimethane and its derivative, a fluorenone derivative, diphenyl dicyanoethylene and its derivative, a diphenoquinone derivative, a metal complex of 8-hydroxyquinoline and its derivative, a polyquinoline and its derivative, a polyquinoxaline and its derivative, a polyfluorene and its derivative, and fullerenes such as $C_{60}$ and their derivatives.

In addition, an organic thin film of the present invention may contain an electric charge generation material to generate an electric charge by a light absorbed in the organic thin film. Electric charge generation materials heretofore known may be used, including an azo compound and its derivative, a diazo compound and its derivative, a non-metal phthalocyanine compound and its derivative, a metal phthalocyanine compound and its derivative, a perylene compound and its derivative, a polycyclic quinone compound and its derivative, a squarylium compound and its derivative, an azulenium compound and its derivative, a thiapyrylium compound and its derivative, and fullerenes such as $C_{60}$ and their derivatives.

Further, an organic thin film of the present invention may contain necessary materials in order to express various functions. Examples of the materials include a sensitizer to intensify a function to generate an electric charge by light absorption, a stabilizer to increase stability, and a UV absorber to absorb a UV light.

In addition, an organic thin film of the present invention may contain a polymer compound material other than the foregoing polymers as a polymer binder in order to increase mechanical characteristics. A polymer binder without excessive impairing effects on an electron transportation property or a hole transportation property is preferable. In addition, a polymer binder having not too strong absorption of a visible light is preferably used.

Examples of the polymer binder like this include poly(N-vinylcarbazole), polyaniline and its derivative, polythiophene and its derivative, poly(p-phenylenevinylene) or its derivative, poly(2,5-thienylenevinylene) and its derivative, polycarbonate, polyacrylate, polymethyl acrylate, polymethyl methacrylate, polystyrene, polyvinyl chloride and polysiloxane.

There is no restriction in a method for producing an organic thin film of the present invention. For example, there may be mentioned the method in which the film is formed by using a solution containing the foregoing polymer which is mixed, as appropriate, with an electron transporting material or a hole transporting material and a polymer binder. In the case that the polymer of the present invention has a subliming property, it may be vapor-deposited in vacuum to form the thin film.

A solvent used to form the film from a solution is not particularly restricted as far as it can dissolve the polymer, an electron transporting material or a hole transporting material, and a polymer binder to be mixed.

Examples of the solvent as mentioned above include unsaturated hydrocarbon solvents such as toluene, xylene, mesitylene, tetraline, decaline, bicyclohexyl, n-butylbenzene, sec-butylbenzene and tert-butylbenzene; halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane; halogenated unsaturated hydrocarbon solvents such as chlorobenzene, dichlorobenzene and trichlorobenzene; and ether solvents such as tetrahydrofurane and tetrahydropyran. The polymer may be dissolved in these solvents with a concentration of usually 0.1% or more by weight, though it depends on a structure and a molecular weight of the polymer.

A method for film formation from a solution includes an application using a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a dispenser printing method, a nozzle coating method, and a capillary coating method. A spin coating method, a flexo printing method, an inkjet printing method, a dispenser printing method, a nozzle coating method and a capillary coating method are preferably used.

A process to produce an organic thin film of the present invention may include a step of orienting an oligomer or a polymer. The organic thin film having oriented polymer compounds by this step improves an electron mobility or a hole mobility because main chain molecules or side chain molecules line up in the same direction.

To orient the polymer compound, heretofore known methods for orienting liquid crystals may be used. Among them, a rubbing method, a photo-alignment method, a shearing method (shear stress application method) and a pull-out coating method are simple, effective and easily applicable as an orientation method, wherein a rubbing method and a shearing method are preferable.

An organic thin film of the present invention may be usable in organic thin film devices such as an organic thin film transistor, an organic solar cell and an optical sensor, by controlling transportation of an electron or a hole injected from an electrode, or an electric charge generated by a light-absorption, because the film has an electron transportation property or a hole transportation property. When an organic thin film of the present invention is used for these organic thin film devices, it is preferable to orient it by the orientation treatment because an electron transportation property or a hole transportation property is further improved.

Then, an application of the organic thin film of the present invention to an organic thin film transistor will be explained. An organic thin film transistor may have a structure comprising a source electrode, a drain electrode, an organic thin film layer (active layer) which serves as an electric channel between these electrodes and contains a polymer of the present invention, and a gate electrode which controls an amount of the electric current running through the electric channel, wherein a field-effect type and a static induction type may be exemplified for it.

It is preferable that the organic thin film transistor of a field-effect type comprise a source electrode, a drain electrode, an organic thin film layer (active layer) which serves as an electric channel between these electrodes and contains a polymer of the present invention, a gate electrode which controls an amount of the electric current running through the electric channel, and an insulator layer formed between the active layer and the gate electrode. It is particularly preferable that the source electrode and the drain electrode are formed in contact with the organic thin film layer (active layer) containing a polymer of the present invention, and in addition, the gate electrode is formed via the insulator layer which is contacted to the organic thin film layer.

It is preferable that the organic thin film transistor of a static induction type comprise a source electrode, a drain electrode, an organic thin film layer which serves as an electric channel between these electrodes and contains a polymer of the present invention, and a gate electrode which controls an amount of the electric current running through the electric channel, in which the gate electrode is formed in the organic thin film layer. It is particularly preferable that the source electrode, the drain electrode, and the gate electrode formed in the organic thin film layer are formed in contact with the organic thin film layer containing a polymer of the present invention. The gate electrode may be adequate as far as it has a structure in which an electric channel from a source electrode to the drain electrode is formed and an amount of the electric current running through the electric channel is controlled by a voltage applied on the gate electrode. A comb-shape electrode may be exemplified for it.

FIG. 1 is a schematic sectional view of the organic thin film transistor (organic thin film transistor of a field-effect type) according to a first embodiment. The organic thin film transistor 100 shown in FIG. 1 comprises a substrate 1; a source electrode 5 and a drain electrode 6 which are formed with a certain distance between them on the substrate 1; an active layer 2 formed on the substrate 1 in such a manner as to cover the source electrode 5 and the drain electrode 6; an insulator layer 3 formed on the active layer 2; and a gate electrode 4 formed on the insulator layer 3 in such a manner as to cover an area between the source electrode 5 and the drain electrode 6 in the insulator layer 3.

Figure 2:
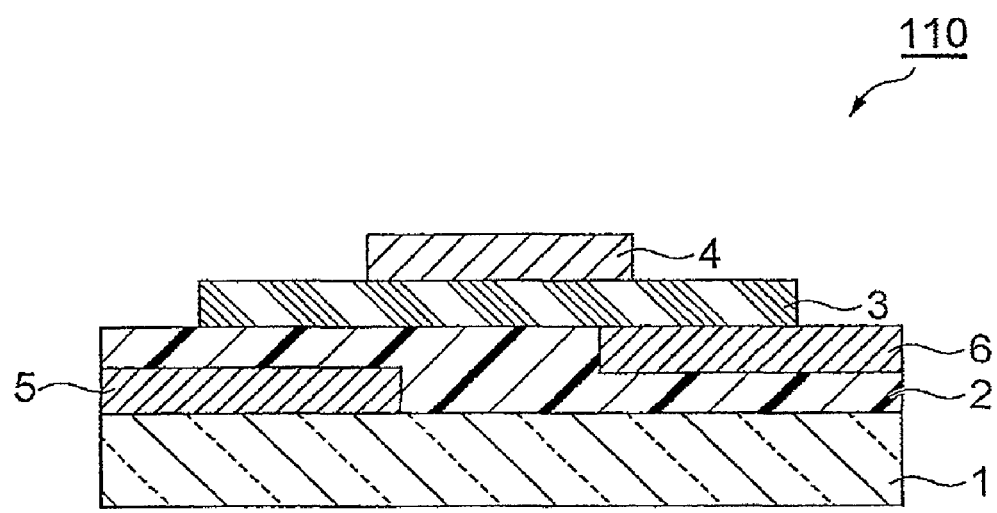
FIG. 2 is a schematic sectional view of the organic thin film transistor according to a second embodiment.

FIG. 2 is a schematic sectional view of the organic thin film transistor (organic thin film transistor of a field-effect type) according to a second embodiment. The organic thin film transistor 110 shown in FIG. 2 comprises a substrate 1; a source electrode 5 formed on the substrate 1; an active layer 2 formed on the substrate 1 in such a manner as to cover the source electrode 5; a drain electrode 6 formed on the active layer 2 with a certain distance from the source electrode 5; an insulator layer 3 formed on the active layer 2 and the drain electrode 6; and a gate electrode 4 formed on the insulator layer 3 in such a manner as to cover an area between the source electrode 5 and the drain electrode 6 in the insulator layer 3.

Figure 3:
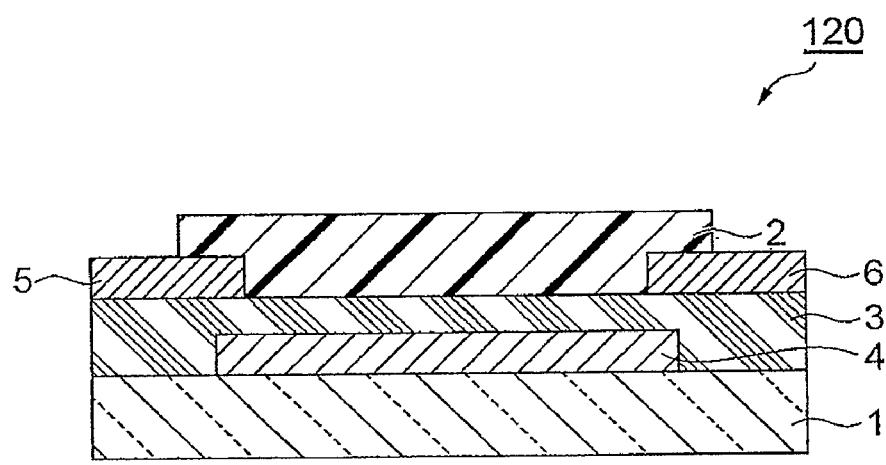
FIG. 3 is a schematic sectional view of the organic thin film transistor according to a third embodiment.

FIG. 3 is a schematic sectional view of the organic thin film transistor (organic thin film transistor of a field-effect type) according to a third embodiment. The organic thin film transistor 120 shown in FIG. 3 comprises a substrate 1; a gate electrode 4 formed on the substrate 1; an insulator layer 3 formed on the substrate 1 in such a manner as to cover the gate electrode 4; a source electrode 5 and a drain electrode 6 formed with a certain distance between them on the insulator layer 3 in such a manner as to cover a part of the area of the insulator layer 3 under which the gate electrode 4 is formed; and an active layer 2 formed on the insulator layer 3 in such a manner as to cover a part of the source electrode 5 and the drain electrode 6.

Figure 4:
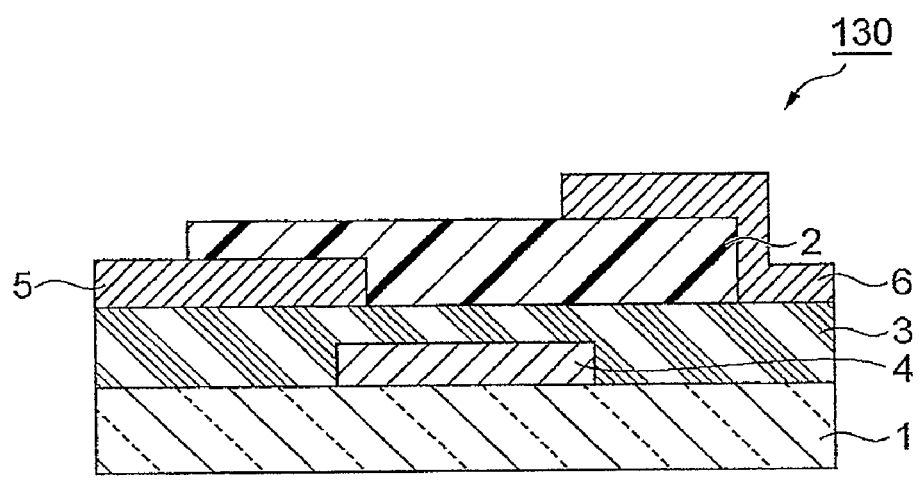
FIG. 4 is a schematic sectional view of the organic thin film transistor according to a fourth embodiment.

FIG. 4 is a schematic sectional view of the organic thin film transistor (organic thin film transistor of a field-effect type) according to a fourth embodiment. The organic thin film transistor 130 shown in FIG. 4 comprises a substrate 1; a gate electrode 4 formed on the substrate 1; an insulator layer 3 formed on the substrate 1 in such a manner as to cover the gate electrode 4; a source electrode 5 formed on the insulator layer 3 in such a manner as to cover a part of the area of the insulator layer 3 under which the gate electrode 4 is formed; an active layer 2 formed on the insulator layer 3 in such a manner as to cover a part of the source electrode 5; and a drain electrode 6 formed on the insulator layer 3 with a certain distance from the source electrode 5 in such a manner as to cover a part of the area of the active layer 2 under which the gate electrode 4 is formed.

Figure 5:
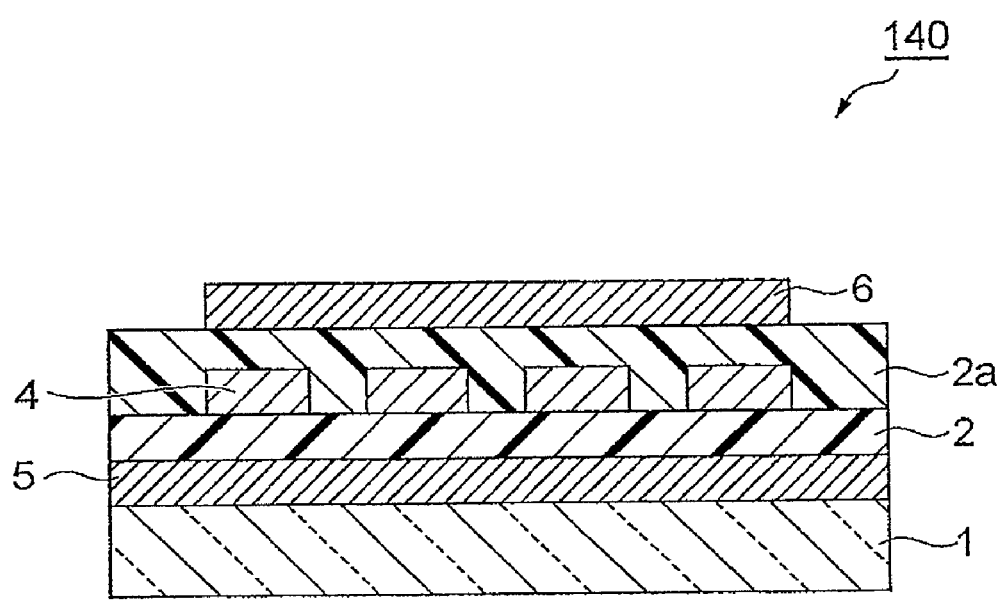
FIG. 5 is a schematic sectional view of the organic thin film transistor according to a fifth embodiment.

FIG. 5 is a schematic sectional view of the organic thin film transistor (organic thin film transistor of a static induction type) according to a fifth embodiment. The organic thin film transistor 140 shown in FIG. 5 comprises a substrate 1; a source electrode 5 formed on the substrate 1; an active layer 2 formed on the source electrode 5; a plurality of gate electrodes 4 formed with certain distances on the active layer 2; an active layer 2a formed on the active layer 2 in such a manner as to cover all of the gate electrodes 4 (a material to form the active layer 2a may be the same as or different from that of the active layer 2); and a drain electrode 6 formed on the active layer 2a.

Figure 6:
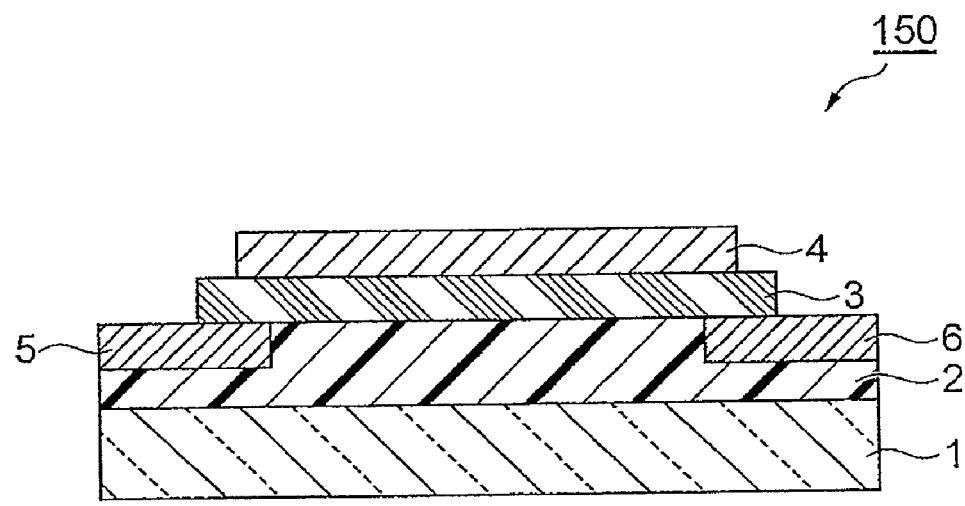
FIG. 6 is a schematic sectional view of the organic thin film transistor according to a sixth embodiment.

FIG. 6 is a schematic sectional view of the organic thin film transistor (organic thin film transistor of a field-effect type) according to a sixth embodiment. The organic thin film transistor 150 shown in FIG. 6 comprises a substrate 1; an active layer 2 formed on the substrate 1; a source electrode 5 and a drain electrode 6 formed with a certain distance between them on the active layer 2; an insulator layer 3 formed on the active layer 2 in such a manner as to cover a part of the source electrode 5 and the drain electrode 6; and a gate electrode 4 formed on the insulator layer 3 in such a manner as to cover each of a part of an area of the insulator layer 3 under which the source electrode 5 is formed and a part of an area of the active layer 3 under which the drain electrode 6 is formed.

Figure 7:
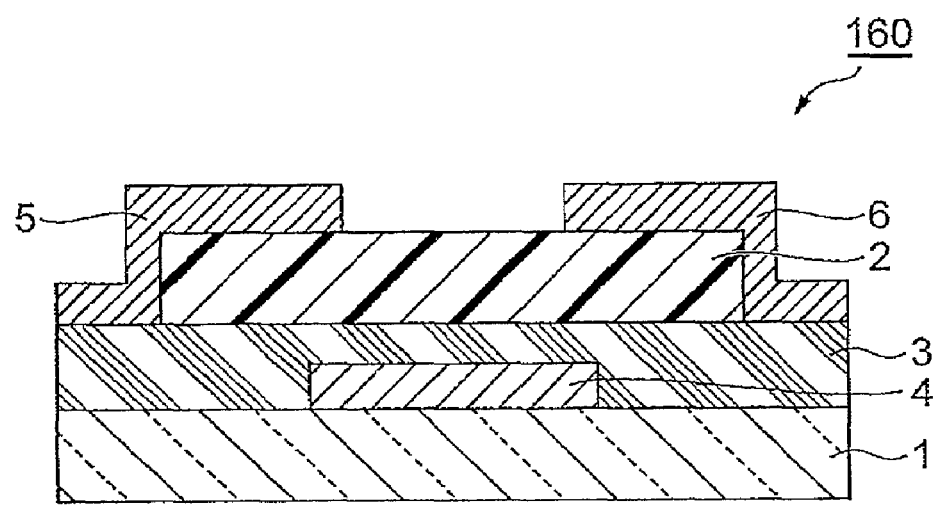
FIG. 7 is a schematic sectional view of the organic thin film transistor according to a seventh embodiment.

FIG. 7 is a schematic sectional view of the organic thin film transistor (organic thin film transistor of a field-effect type) according to a seventh embodiment. The organic thin film transistor 160 shown in FIG. 7 comprises a substrate 1; a gate electrode 4 formed on the substrate 1; an insulator layer 3 formed on the substrate 1 in such a manner as to cover the gate electrode 4; an active layer 2 formed in such a manner as to cover an area of the insulator layer 3 under which the gate electrode 4 is formed; a source electrode 5 formed on the insulator layer 3 in such a manner as to cover a part of the area of the active layer 2 under which the gate electrode 4 is formed; and a drain electrode 6 formed on the insulator layer 3 with a certain distance from the source electrode 5 in such a manner as to cover a part of the area of the active layer 2 under which the gate electrode 4 is formed.

In the organic thin film transistors according to the first to the seventh embodiments, the active layer 2 and/or the active layer 2a contain(s) a polymer of the present invention, and serves as an electric channel between the source electrode 5 and the drain electrode 6. The gate electrode 4 controls an amount of the electric current running through the electric channel in the active layer 2 and/or the active layer 2a by applying a voltage.

The organic thin film transistor of a field-effect type as mentioned above may be produced by heretofore known methods, for example, a method described in JP 05-110069 A. The organic thin film transistor of a static induction type as mentioned above may be produced by heretofore known methods, for example, a method described in JP 2004-006476 A.

The substrate 1 is not particularly restricted as far as the characteristics as an organic thin film transistor are not impaired, and a glass substrate, a flexible film substrate and a plastic substrate may be used for it.

Because a use of the compound which is soluble in an organic solvent is highly advantageous and preferable in production of the active layer 2, the organic thin film which becomes the active layer 2 may be formed by the method for producing an organic thin film of the present invention as mentioned above.

The insulator layer 3 in contact with the active layer 2 is not particularly restricted as far as a material for it has a high electric insulating property, and heretofore known materials may be used for it. Examples of the materials to form the insulator layer 3 include SiOx, SiNx, Ta$_2$O$_5$, polyimide, polyvinyl alcohol, polyvinyl phenol, an organic glass and a photoresist. In view of a trend to a lower voltage, a material having a high dielectric constant is preferable.

In the case that the active layer 2 is formed on the insulator layer 3, in order to improve an interfacial characteristics of the insulator layer 3 and the active layer 2, the active layer 2 may be formed after a surface of the insulator layer 3 is treated for surface modification with a surface-treating agent such as a silane-coupling agent. Examples of the surface-treating agent include a long chain alkyl chlorosilane, a long chain alkyl alkoxysilane, a fluorinated alkyl chlorosilane, a fluorinated alkyl alkoxysilane, and a silylamine compound such as hexamethyl disilazane. Prior to the treatment by a surface-treating agent, it may also be possible to treat the insulator layer surface by an ozone UV or an O$_2$ plasma.

Further, after formation of an organic thin film transistor, it is preferable to form a protection film on the organic thin film transistor to protect the device. With this, the organic thin film transistor is shielded from an atmosphere so that decrease in characteristics of the organic thin film transistor may be suppressed. In addition, an effect from the step of forming a display device that drives on the organic thin film transistor may be reduced by the protection film.

As a method for forming the protection film, there may be mentioned the method in which a covering is made by a UV-curable resin, a thermosetting resin or an inorganic SiONx film. In order to effectively shield from an atmosphere, it is preferable to carry out the steps after formation of the organic thin film transistor till formation of the protection film without exposing it to an atmosphere (for example, under a dry nitrogen atmosphere, or under vacuum).

Figure 8:
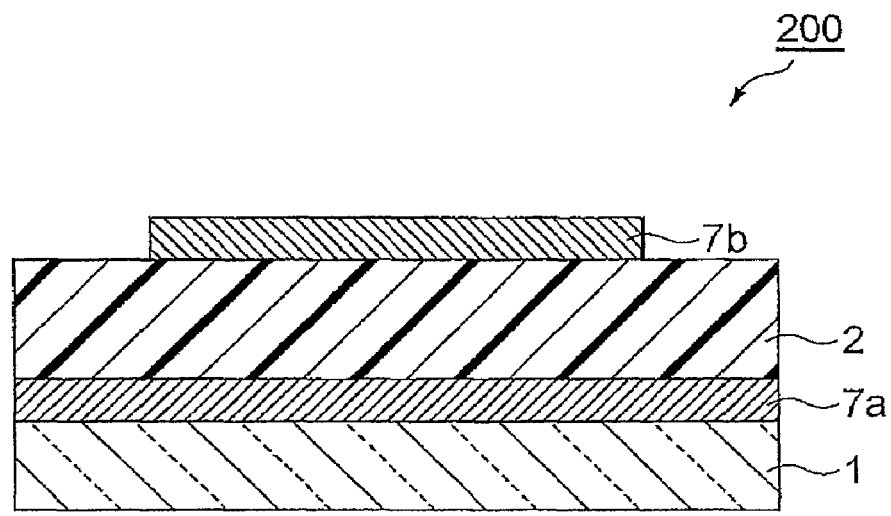
FIG. 8 is a schematic sectional view of the solar cell according to an embodiment.

Then, an application of the organic thin film of the present invention to a solar cell will be explained. FIG. 8 is a schematic sectional view of a solar cell according to an embodiment. The solar cell 200 shown in FIG. 8 comprises a substrate 1; a first electrode 7a formed on the substrate 1; an active layer 2 comprising an organic thin film containing a polymer of the present invention formed on the first electrode 7a; and a second electrode 7b formed on the active layer 2.

In the solar cell according to the embodiment, a transparent or a translucent electrode is used in one of the first electrode 7a and the second electrode 7b. As a material for the electrodes, a metal such as aluminum, gold, silver, copper, an alkaline metal and an alkaline earth metal, or their translucent film or transparent electric conductive film may be used. In order to have a high open voltage, it is preferable to select each electrode in such a way as to give a large difference in work functions. The active layer 2 (organic thin film) may be used with addition of an electric charge generator and a sensitizer in order to enhance a photo-sensitivity. As the substrate 1, for example, a silicon substrate, a glass substrate or a plastic substrate may be used.

Figure 9:
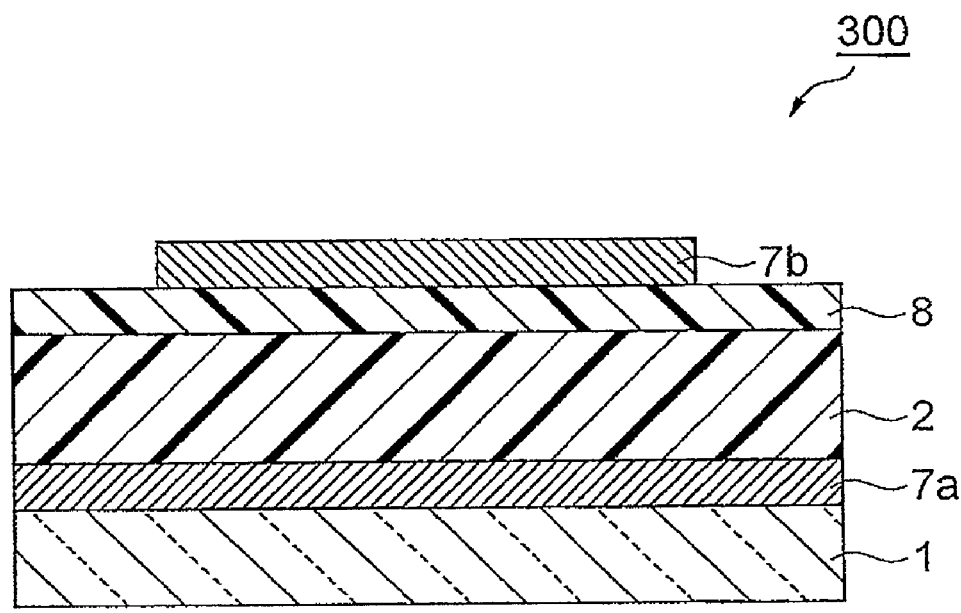
FIG. 9 is a schematic sectional view of the optical sensor according to the first embodiment.

Then, an application of the organic thin film of the present invention to an optical sensor will be explained. FIG. 9 is a schematic sectional view of the optical sensor according to the first embodiment. The optical sensor 300 shown in FIG. 9 comprises a substrate 1; a first electrode 7a formed on the substrate 1; an active layer 2 comprising an organic thin film containing a polymer of the present invention formed on the first electrode 7a; an electric charge generator layer 8 formed on the active layer 2; and a second electrode 7b formed on the electric charge generator layer 8.

Figure 10:
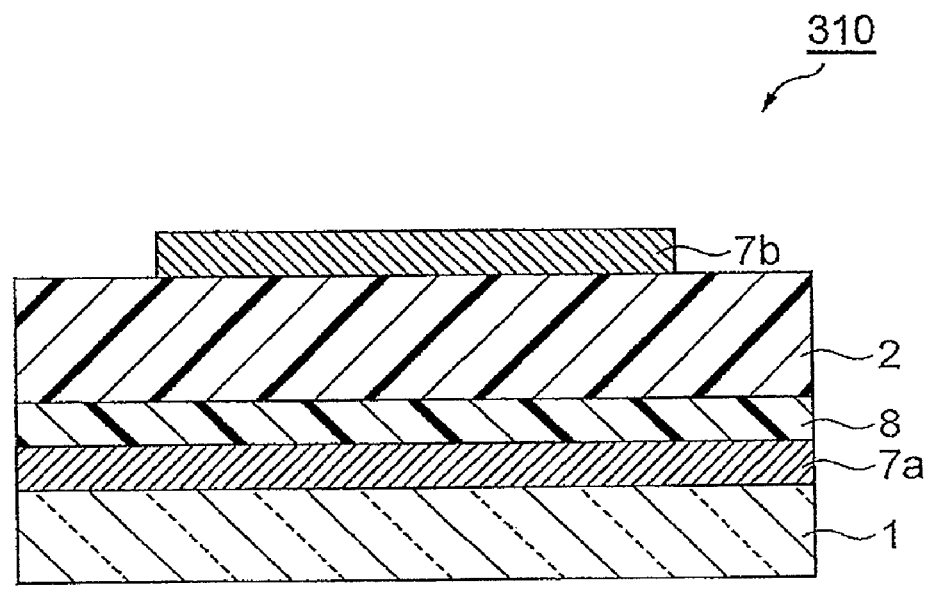
FIG. 10 is a schematic sectional view of the optical sensor according to the second embodiment.

FIG. 10 is a schematic sectional view of the optical sensor according to the second embodiment. The optical sensor 310 shown in FIG. 10 comprises a substrate 1; a first electrode 7a formed on the substrate 1; an electric charge generator layer 8 formed on the first electrode 7a; an active layer 2 comprising an organic thin film containing a polymer of the present invention formed on the electric charge generator layer 8; and a second electrode 7b formed on the active layer 2.

Figure 11:
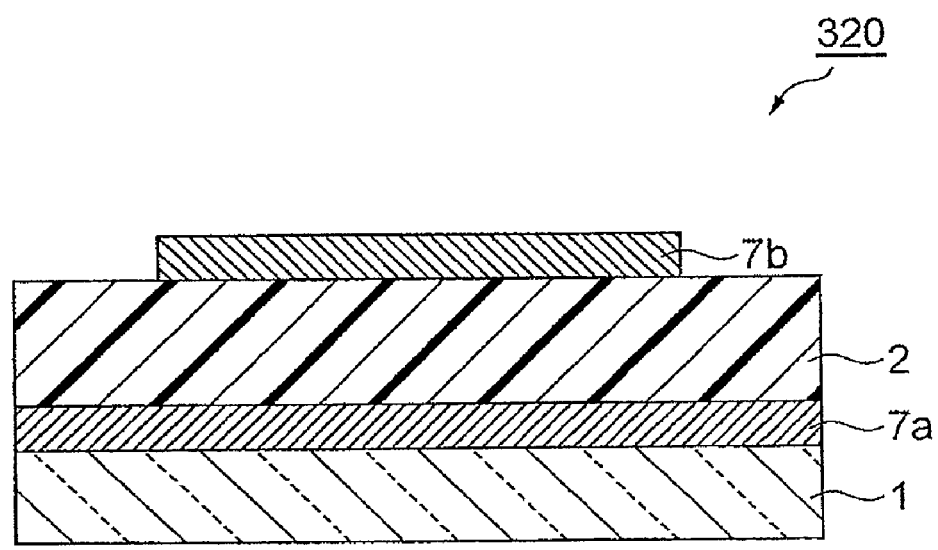
FIG. 11 is a schematic sectional view of the optical sensor according to the third embodiment.

FIG. 11 is a schematic sectional view of the optical sensor according to the third embodiment. The optical sensor 320 shown in FIG. 11 comprises a substrate 1; a first electrode 7a formed on the substrate 1; an active layer 2 comprising an organic thin film containing a polymer of the present invention formed on the first electrode 7a; and a second electrode 7b formed on the active layer 2.

In the optical sensor according to the first to the third embodiments, a transparent or a translucent electrode is used in one of the first electrode 7a and the second electrode 7b. The electric charge generator layer 8 is a layer generating an electric charge by absorbing a light. As a material for the electrodes, a metal such as aluminum, gold, silver, copper, an alkaline metal and an alkaline earth metal, or their translucent film or transparent electric conductive film may be used. The active layer 2 (organic thin film) may contain a carrier generator, a sensitizer and the like in order to enhance a photo-sensitivity. As the substrate 1, for example, a silicon substrate, a glass substrate or a plastic substrate may be used.

In the above, the present invention has been explained in detail by embodiments. However, the present invention is not limited to the foregoing embodiments. The present invention can be variously modified within its scope.

EXAMPLES

Hereinbelow, the present invention will be explained specifically by Examples, but the present invention is by no means limited to the following Examples.

Conditions for Measurements and the Like

Spectrum of nuclear magnetic resonance (NMR) was measured by JMN-270 (trade name, manufactured by JEOL, Ltd.) with 270 MHz for measurement of $^1$H, or JMNLA-600 (trade name, manufactured by JEOL, Ltd.) with 600 MHz for measurement of $^{19}$F. Chemical shifts are shown by parts per million (ppm). Tetramethyl silane (TMS) was used as the internal standard of 0 ppm. Coupling constants (J) are shown by Hertz, wherein abbreviations s, d, t, q, m and br mean singlet, doublet, triplet, quartet, multiplet and broad, respectively. Mass analysis (MS) was measured by GCMS-QP5050A (trade name, manufactured by Shimadzu Corporation) with an electron ionization (EI) method and a direct injection (DI) method. Silica gel used for a column chromatography separation was Silica Gel 60N (trade name, manufactured by Kanto Chemical Co., Inc.) with 40 to 50 μm in size. All chemical substances were of reagent grades, and purchased from Wako Pure Chemicals Industries, Ltd., Tokyo Chemical Industry Co., Ltd., Kanto Chemical Co., Inc., Nacalai Tesque, Inc., Sigma Aldrich Japan K. K., or Daikin Chemicals Sales, Ltd.

Cyclic voltammetry was measured by CV-50W (trade name, manufactured by BAS, Inc.) with a Pt work electrode (manufactured by BAS, Inc.), a Pt line counter electrode, and an Ag reference electrode. Measurements were made with a sweeping rate of 100 mV/second and a scanning potential ranging from −2.8 to 1.6 V. Reduction potential and oxidation potential were measured with a completely dissolved solution of a polymer (1×10$^{-3}$ mol/liter) and tetrabutyl ammonium hexafluorophosphate (TBAPF6) (0.1 mol/liter) as a supporting electrolyte in monofluorobenzene solvent.

Reference Synthesis Example 1

<Synthesis of Compound A>

A starting raw material 1,3-dibromo-4H-cyclopenta[c]thiophene-4,6(5H)-dione was synthesized according to the report by Khanh, L. P., Dallemagne, P., and Rault, S. Synlett., 1999, 9, 1450-1452. Then, an ethyl acetate solution (5 mL) of 1,3-dibromo-4H-cyclopenta[c]thiophene-4,6(5H)-dione (1.00 g, 3.25 mmol) and N-fluoro-6-(trifluoromethyl)pyridinium-2-sulfonate (MEC-04B) (1.75 g, 7.14 mmol) was prepared and agitated at 85° C. for 4 hours. After the reaction solution was cooled to a room temperature, it was poured into water and then extracted by ethyl acetate. The organic layer formed after the extraction was washed by saturated sodium chloride water and dried by anhydrous sodium sulfate. After insoluble matters were removed by filtration, the solvent was distilled out under a reduced pressure. The residue obtained was purified by a column chromatography using a silica gel (hexane/chloroform=1/1) to obtain "1,3-dibromo-5,5-difluoro-4H-cyclopenta[c]thiophene-4,6(5H)-dione" shown by the following formula (40) (hereinafter referred to as "Compound A") (Yield 1.53 g, 75%).

[Chemical Formula 35]

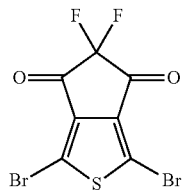

(40)

Example 1

<Synthesis of Polymer A>

The foregoing Compound A (589 mg, 1.70 mmol), 2-tributyl stannyl thiophene (1.32. g, 5.10 mmol), and tetrakis(triphenylphosphine)palladium(0) (196 mg, 0.17 mmol) were taken into a test tube having a cap which had been dried by heating. Then, toluene (10 mL) was added to it, and the reaction was carried out at 120° C. After 12 hours, the resulting mixture was allowed to be cooled and extracted by ethyl acetate. The organic layer was dried by anhydrous sodium sulfate and filtered. After concentration under a reduced pressure, the residue obtained was purified by a column chromatography (silica gel charged by chloroform) by using a developing solvent (hexane/ethyl acetate=4/1) to obtain an intended Polymer A (186 mg, 31%) as shown by the following formula (41) as a red solid. Reduction potential of Polymer A was −1.39 V.

TLC R$_f$=0.44 (4:1 hexane/EtOAc): $^1$H-NMR (270 MHz, CDCl$_3$) δ 8.17-8.19 (m, 2H), 7.55-7.57 (m, 2H), 7.18-7.22 (m, 2H): MS (EI) m/z 352 (M$^+$).

[Chemical Formula 36]

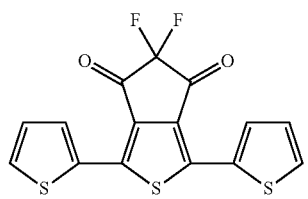

(41)

Example 2

<Synthesis of Polymer B>

Compound A (160 mg, 0.463 mmol), phenyl boric acid (56 mg, 0.463 mmol), potassium carbonate (128 mg, 0.925 mmol), and tetrakis(triphenylphosphine)palladium(0) (53 mg, 0.046 mmol) were taken into a test tube having a cap which had been dried by heating. Then, the resulting mixture was dissolved into THF/water=5/1 (5 mL) and reacted at 90° C. After 12 hours, the mixture was allowed to be cooled and extracted by ethyl acetate. The organic layer was dried by anhydrous sodium sulfate and filtered. After concentration under a reduced pressure, the residue obtained was purified by a column chromatography (silica gel charged by chloroform) by using a developing solvent (hexane/ethyl acetate=4/1) to obtain an intended Polymer B (73 mg, 46%) as shown by the following formula (42) as a yellow solid. Reduction potential of Polymer B was −1.41 V.

TLC R$_f$=0.50 (4:1 hexane/EtOAc): $^1$H-NMR (270 MHz, CDCl$_3$) δ 8.05-8.07 (m, 4H), 7.53-7.55 (m, 6H): MS (EI) m/z 340 (M$^+$).

[Chemical Formula 37]

(42)

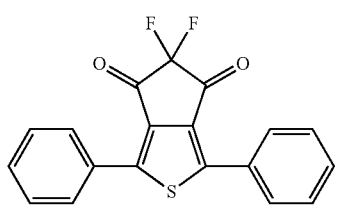

Example 3

<Synthesis of Polymer C>

The foregoing Polymer A is dissolved in chloroform in a round bottom flask, and then bistrifluoroacetic acid/iodobenzene and iodine are added to it at 0° C. for reaction. The reaction is quenched by adding a saturated sodium thiosulfate aqueous solution. After extraction by chloroform, the reaction mixture is subjected to a column chromatography for purification to obtain an intended Polymer C as shown by the following formula (43).

[Chemical Formula 38]

(43)

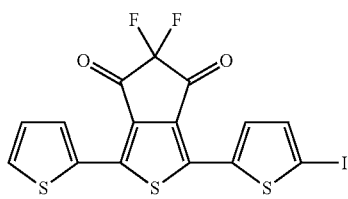

Example 4

<Synthesis of Polymer D>

Into a test tube having a cap which has been dried by heating, the foregoing Polymer C, palladium(II) acetate, and diisopropyl amine are taken and reacted in toluene at 120° C. The reaction mixture is subjected to a column chromatography for purification to obtain an intended Polymer D as shown by the following formula (44).

[Chemical Formula 39]

(44)

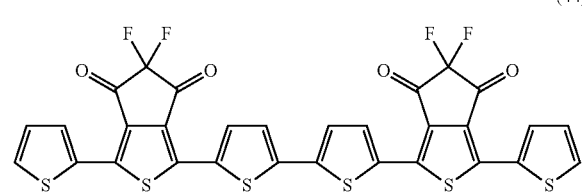

Example 5

<Synthesis of Polymer E>

Into a test tube having a cap which has been dried by heating, Compound A, 5-tributylstannyl-2-phenylthiophene, and tetrakis(triphenylphosphine)palladium(0) are taken and reacted in toluene at 120° C. The reaction mixture is subjected to a column chromatography for purification to obtain an intended Polymer E as shown by the following formula (45).

[Chemical Formula 40]

(45)

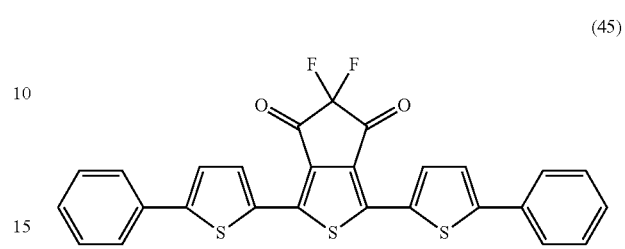

Example 6

<Synthesis of Polymer F>

Into a test tube having a cap which has been dried by heating, Compound A, 5-tributylstannyl-2-(4-acetylphenyl)thiophene, and tetrakis(triphenylphosphine)palladium(0) are taken and reacted in toluene at 120° C. The reaction mixture is subjected to a column chromatography for purification to obtain an intended Polymer F as shown by the following formula (46).

[Chemical Formula 41]

(46)

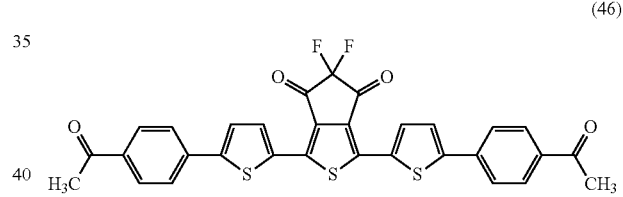

Example 7

<Synthesis of Polymer G>

Into a test tube having a cap which has been dried by heating, Compound A, 5-tributylstannyl-2-(4-trifluoroacetylphenyl)thiophene, and tetrakis(triphenylphosphine)palladium(0) are taken and reacted in toluene at 120° C. The reaction mixture is subjected to a column chromatography for purification to obtain an intended Polymer G as shown by the following formula (47).

[Chemical Formula 42]

(47)

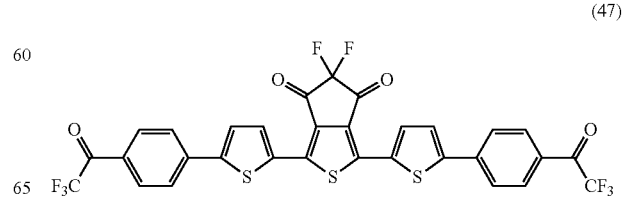

Example 8

<Synthesis of Polymer H>

Into a test tube having a cap which has been dried by heating, Compound A, 4-(5-tributylstannylthiophene-2-yl)benzamide, and tetrakis(triphenylphosphine)palladium(0) are taken and reacted in toluene at 120° C. The reaction mixture is subjected to a column chromatography for purification to obtain an intended Polymer H as shown by the following formula (48).

[Chemical Formula 43]

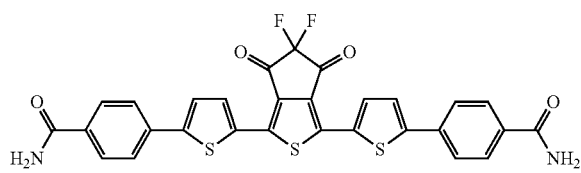

(48)

Example 9

<Synthesis of Polymer I>

Into a test tube having a cap which has been dried by heating, Compound A, 2-acetyl-5-tributylstannyl thiophene, and tetrakis(triphenylphosphine)palladium(0) are taken and reacted in toluene at 120° C. The reaction mixture is subjected to a column chromatography for purification to obtain an intended Polymer I as shown by the following formula (49).

[Chemical Formula 44]

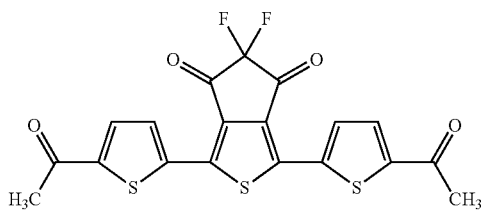

(49)

Example 10

<Synthesis of Polymer J>

Into a test tube having a cap which has been dried by heating, Compound A, 5-tributylstannyl-2-trifluoroacetyl thiophene, and tetrakis(triphenylphosphine)palladium(0) are taken and reacted in toluene at 120° C. The reaction mixture is subjected to a column chromatography for purification to obtain an intended Polymer J as shown by the following formula (50).

[Chemical Formula 45]

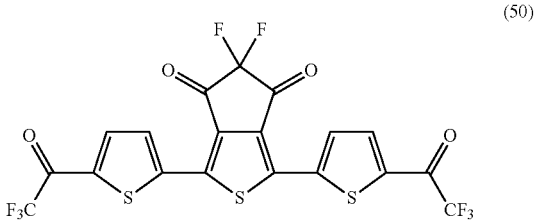

(50)

Example 11

<Synthesis of Polymer K>

Into a test tube having a cap which has been dried by heating, Compound A, 5-tributylstannylthiophene-2-carboamide, and tetrakis(triphenylphosphine)palladium(0) are taken and reacted in toluene at 120° C. The reaction mixture is subjected to a column chromatography for purification to obtain an intended Polymer K as shown by the following formula (51).

[Chemical Formula 46]

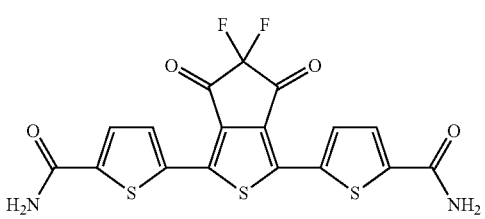

(51)

Example 12

<Synthesis of Polymer L>

Into a test tube having a cap which has been dried by heating, Compound A, 2,5-bis(tributylstannyl)thiophene, and tetrakis(triphenylphosphine)palladium(0) are taken and reacted in toluene at 120° C. The reaction mixture is subjected to a column chromatography for purification to obtain an intended Polymer L as shown by the following formula (52).

[Chemical Formula 47]

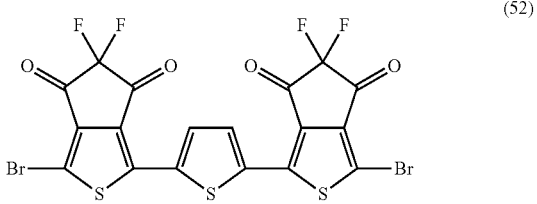

(52)

Example 13

<Synthesis of Polymer M>

Into a test tube having a cap which has been dried by heating, Polymer L, phenyl boric acid, potassium carbonate, and tetrakis(triphenylphosphine)palladium(0) are taken and reacted in a THF/water mixture solvent at 90° C. The reaction mixture is subjected to a column chromatography for purification to obtain an intended Polymer M as shown by the following formula (53).

[Chemical Formula 48]

(53)

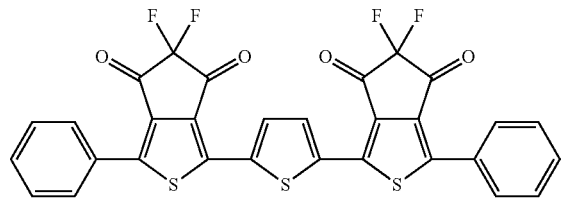

Example 14

<Synthesis of Polymer N>

Into a test tube having a cap which has been dried by heating, Polymer L, 4-acetylphenyl boric acid, potassium carbonate, and tetrakis(triphenylphosphine)palladium(0) are taken and reacted in a THF/water mixture solvent at 90° C. The reaction mixture is subjected to a column chromatography for purification to obtain an intended Polymer N as shown by the following formula (54).

[Chemical Formula 49]

(54)

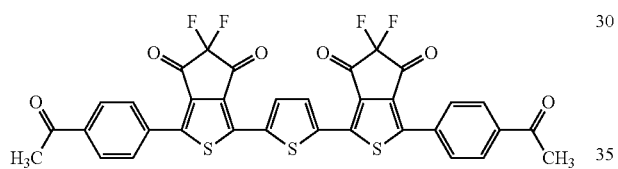

Example 15

<Synthesis of Polymer P>

Into a test tube having a cap which has been dried by heating, Polymer L, 4-trifluoroacetylphenyl boric acid, potassium carbonate, and tetrakis(triphenylphosphine)palladium (0) are taken and reacted in a THF/water mixture solvent at 90° C. The reaction mixture is subjected to a column chromatography for purification to obtain an intended Polymer P as shown by the following formula (55).

[Chemical Formula 50]

(55)

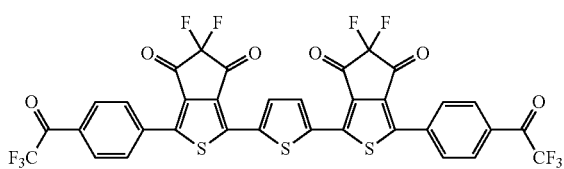

Example 16

<Synthesis of Polymer Q>

Polymer A is dissolved in DMF in a round bottom flask, and then N-bromosuccinimide is added to carry out the reaction. The reaction mixture is subjected to a column chromatography for purification to obtain an intended Polymer Q as shown by the following formula (56).

[Chemical Formula 51]

(56)

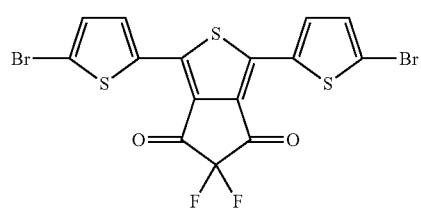

Example 17

<Synthesis of Polymer R>

Into a nitrogen-replaced 50-mL Shlenk flask, 2,7-bis(tributylstannyl)-9,9-dioctyl fluorene, Polymer Q, and dichlorobis (triphenylphosphine)palladium are taken. After 3 mL of DMF is added to it, the resulting mixture is heated to 150° C. and agitated for 24 hours. Then, THF is added and agitation is continued further 48 hours. After the mixture is cooled to a room temperature, an intended polymer R as shown by the following formula (57) is obtained by reprecipitation from a mixed methanol/water (1/1).

[Chemical Formula 52]

(57)

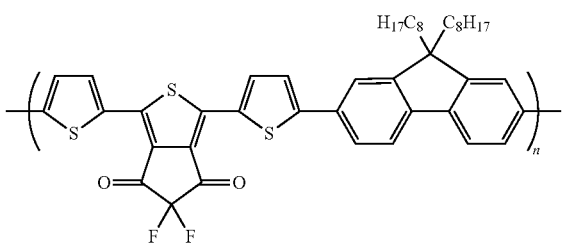

Example 18

<Synthesis of Polymer S>

Into a test tube having a cap, Compound A, 2,7-dibromo-9,9-dioctyl fluorene, tris(dibenzylideneacetone)dipalladium, and tri(o-tolyl)phosphine are taken under an argon stream. After chlorobenzene (5 mL) is added to it, a reaction is carried out at 105° C. After 8 hours, the reaction mixture is allowed to be cooled and then poured into a mixed solution of methanol (50 mL) and 37 wt % of concentrated hydrochloric acid (5 mL). After the resulting mixture is agitated for 30 minutes, a precipitated polymer is collected by filtration though a Kiriyama rohto filter and then washed with methanol and then by acetone to obtain an intended Polymer S as shown by the following formula (58).

[Chemical Formula 53]

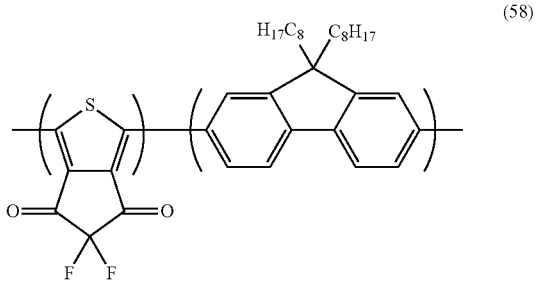

(58)

Example 19

<Preparation of Organic Thin Film Device 1 and Evaluation of its Solar Cell Characteristics>

Each of Polymer A prepared in Example 1 and poly(3-hexylthiophene) (P3HT, manufactured by Aldrich Chemical Co.) was dissolved into o-dichlorobenzene (concentration of 2.0% by weight each), and they were filtered through a 0.2 μm membrane filter. The solution of Polymer A and the solution of P3HT were mixed at the ratio of 1 to 1 by volume to obtain a solution for coating. The solution thus obtained was coated by a spin coating method to a glass substrate having a 150-nm thickness ITO film formed by a spattering method to give an organic thin film with a thickness of 70 nm. Onto the foregoing organic thin film, lithium fluoride was vapor-deposited with a thickness of 4 nm equivalent by a vacuum deposition method. On it, aluminum was vapor-deposited with a thickness of 70 nm. Then, a glass plate was sealed further on it by adhering with a UV-curable resin to obtain an organic thin film device 1 comprising Polymer A. The obtained organic thin film device 1 was irradiated with AM 1.5 (100 mV/cm$^2$) of a quasi-solar light using a solar simulator while measuring voltage-current characteristics. As a result, it was found that Polymer A functions as an n-type semiconductor with a high electron transportation property, and the solar cell characteristics with a short-circuit current of 70 μA/cm$^2$ and an open-circuit voltage of 0.57 V are obtained.

Example 20

<Evaluation of Optical Sensor>

By using the organic thin film device 1 prepared in Example 19, a photocurrent with irradiation of a 200-lux white light and a dark current without the irradiation were measured. As a result, 7.6×10$^2$ was obtained as a current ratio of the photocurrent to the dark current with the application voltage of −0.5 V, and it was confirmed that Polymer A functioned as an n-type semiconductor with a high electron transportation property and the organic thin film device 1 worked as an optical sensor.

Example 21

<Preparation of Organic Thin Film Device 2 and Evaluation of its Transistor Characteristics>

A substrate wherein a silicon oxide film which forms an insulator layer by thermal oxidation is formed on surface of an n-type silicon substrate doped with a high concentration that function as a gate electrode is prepared. Thus prepared substrate is immersed in hexamethyldisilazane (HMDS) at 50° C. for treatment of the silicon oxide film surface. Then, on this surface-treated substrate, an organic thin film of Polymer A is deposited by a vacuum deposition method. On this organic thin film, Au is vapor-deposited through a shadow mask to form a source electrode and a drain electrode to prepare an organic thin film device 2. The transistor characteristics of the organic thin film device 2 thus obtained are measured by varying a gate voltage (Vg) and a source-drain voltage (Vsd) under vacuum. Polymer A that functions as an n-type semiconductor with a high electron transportation property with excellent Id-Vg characteristics is obtained.

Comparative Example 1

<Synthesis of Polymer T>

1,3-Dibromo-cyclopenta[c]thiophene-4,6(5H)-dione (50 mg, 0.161 mmol), thiophene boric acid (59 mg, 0.455 mmol), potassium carbonate (88 mg, 0.637 mmol), and tetrakis(triphenylphosphine)palladium(0) (18 mg, 0.17 mmol) were taken into a test tube having a cap which had been dried by heating. Then, the resulting mixture was dissolved into THF/water=5/1 (1.4 mL) and reacted at 90° C. for 12 hours. The reaction solution was allowed to be cooled and extracted by ethyl acetate. The organic layer was dried by anhydrous sodium sulfate and filtered. After concentration under a reduced pressure, the residue obtained was purified by a column chromatography (silica gel charged by chloroform) by using a developing solvent (hexane/ethyl acetate=4/1) to obtain an intended Polymer T (10 mg, 20%) as shown by the following formula (59) as a yellow solid. Reduction potential of Polymer T was −1.63 V.

TLC R$_f$=0.42 (4:1 hexane/EtOAc): $^1$H-NMR (270 MHz, CDCl$_3$) δ 8.08-8.09 (m, 2H), 7.45-7.47 (m, 2H), 7.14-7.16 (m, 2H), 3,61 (s, 2H): MS (EI) m/z 316 (M$^+$).

[Chemical Formula 54]

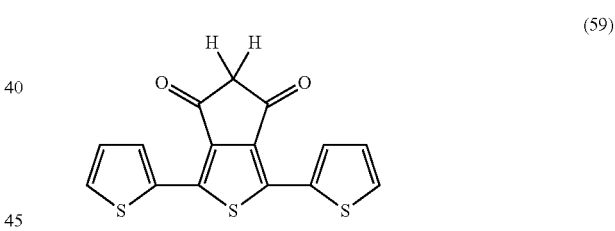

(59)

INDUSTRIAL APPLICABILITY

According to the present invention, a novel polymer usable as an organic n-type semiconductor having an excellent electron transportation property can be provided. In addition, an organic thin film containing this novel polymer and an organic thin film device comprising this organic thin film can be provided. In particular, a novel polymer having a structure of 5,5-difluoro-5,6-dihydro-4H-cyclopenta[c]thiophene-4,6-dione has a lowered LUMO level due to an introduction of the 2,2-difluoro-1,3-cyclopentanedione skeleton and an improved solubility in an organic solvent, and keeps a planarity of the π-conjugation. Accordingly, the foregoing novel polymer is useful as an organic n-type semiconductor having an extraordinarily excellent electron transportation property. Further, this novel polymer can be obtained easily by oligomerization or polymerization of a raw material for it. A polymer of the present invention thus obtained is useful especially for production of an organic transistor, an organic solar cell, an optical sensor and the like. In addition, the foregoing polymer is excellent in an electron transportation property, and thus, the organic thin film transistor comprising the foregoing organic thin film usually shows excellent Id-Vg characteristics, the organic solar cell usually shows excellent voltage-current characteristics, and the optical sensor usually shows an excellent ratio of a photocurrent to a dark current.

The invention claimed is:

1. A polymer having a repeating unit represented by the following general formula (I) and a ferrocene-based reduction potential of −1.5 to −0.5 V as measured by a cyclic voltammetry method:

[Chemical Formula 1]

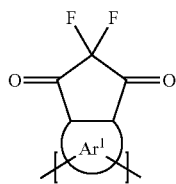
(I)

wherein $Ar^1$ represents a divalent aromatic hydrocarbon group or a divalent heterocyclic group; and these groups may have a substituent.

2. The polymer according to claim 1, wherein the repeating unit represented by the general formula (I) is a repeating unit represented by the following general formula (II):

[Chemical Formula 2]

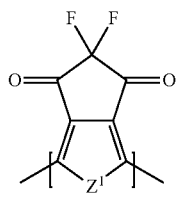
(II)

wherein $Z^1$ represents any one of groups shown by the following formulae (i) to (ix) in which $R^1$, $R^2$, $R^3$ and $R^4$ each independently represents a hydrogen atom or a substituent; and $R^2$ and $R^3$ may be bonded with each other to form a ring:

[Chemical Formula 3]

(i)

(ii)

(iii)

(iv)

(v)

(vi)

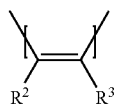
(vii)

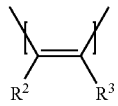
(viii)

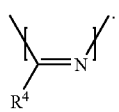
(ix)

3. The polymer according to claim 1, comprising a repeating unit represented by the general formula (I) and a repeating unit represented by the following general formula (III) which is different from the repeating unit represented by the general formula (I):

[Chemical Formula 4]

(III)

wherein $Ar^2$ represents a divalent aromatic hydrocarbon group or a divalent heterocyclic group, and these groups may have a substituent.

4. The polymer according to claim 3, wherein the repeating unit represented by the general formula (III) is a repeating unit represented by the following general formula (IV):

[Chemical Formula 5]

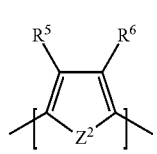
(IV)

wherein $Z^2$ represents any one of groups shown by the following formulae (i) to (ix) In which $R^1$, $R^2$, $R^3$ and $R^4$ each independently represents a hydrogen atom or a substituent, provided that $R^2$ and $R^3$ may be bonded with each other to form a ring; and $R^5$ and $R^6$ in formula (IV) each independently represents a hydrogen atom or a substituent; and $R^5$ and $R^6$ may form a ring:

[Chemical Formula 6]

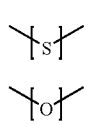
(i)

(ii)

 (iii)

 (iv)

 (v)

 (vi)

 (vii)

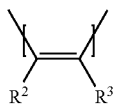 (viii)

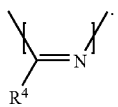 (ix)

5. The polymer according to claim 2, wherein the $Z^1$ represents a group shown by the formula (i).

6. The polymer according to claim 4, wherein the $Z^2$ is the group shown by the formula (i).

7. The polymer according to claim 2, comprising a repeating unit represented by the following general formula (IIa), and a repeating unit represented by the following general formula (IVa) and/or a repeating unit represented by the following general formula (XX):

[Chemical Formula 7]

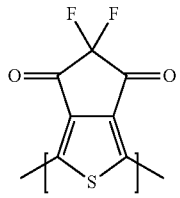 (IIa)

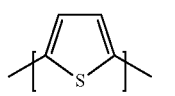 (IVa)

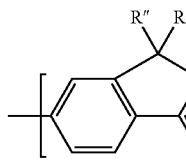 (XX)

wherein in formula (XX), R" represents a hydrogen atom, a fluorine atom, an alkyl group, or an aryl group; and two R" may be the same or different.

8. An organic thin film comprising a polymer according to claim 1 and having a film thickness of 1 nm to 100 μm.

9. The organic thin film according to claim 8, wherein the film is formed by a vacuum deposition method, a spin coating method, an inkjet printing method, a dispenser printing method, a flexo printing method, a nozzle coating method, or a capillary coating method.

10. An organic thin film device comprising an organic thin film according to claim 8.

11. An organic thin film transistor comprising a source electrode and a drain electrode, an organic semiconductor layer serving as an electric channel between these electrodes, and a gate electrode controlling the amount of electric current running through the electric channel, wherein the organic semiconductor layer comprises an organic thin film according to claim 8.

12. An organic solar cell comprising an organic thin film according to claim 8.

13. An optical sensor comprising an organic thin film according to claim 8.

* * * * *